US012778584B2

(12) United States Patent
Lin

(10) Patent No.: US 12,778,584 B2
(45) Date of Patent: Nov. 3, 2026

(54) VASCULAR ANASTOMOSIS DEVICE

(71) Applicant: Hsiu-Feng Lin, Taipei City (TW)

(72) Inventor: Hsiu-Feng Lin, Taipei City (TW)

( * ) Notice: Subject to any disclaimer, the term of this patent is extended or adjusted under 35 U.S.C. 154(b) by 981 days.

(21) Appl. No.: 18/089,049

(22) Filed: Dec. 27, 2022

(65) Prior Publication Data

US 2023/0200814 A1 Jun. 29, 2023

(30) Foreign Application Priority Data

Dec. 27, 2021 (TW) ................................ 110148968

(51) Int. Cl.
*A61B 17/11* (2006.01)

(52) U.S. Cl.
CPC ....... *A61B 17/11* (2013.01); *A61B 2017/1107* (2013.01)

(58) Field of Classification Search
CPC ............ A61B 17/11; A61B 2017/1107; A61B 2017/1132
See application file for complete search history.

(56) References Cited

U.S. PATENT DOCUMENTS

| | | | | |
|---|---|---|---|---|
| 5,695,504 A * | 12/1997 | Gifford, III | A61B 17/12045 | 606/139 |
| 7,901,417 B2 * | 3/2011 | Blatter | A61B 17/11 | 606/151 |
| 8,372,088 B2 * | 2/2013 | Morsi | A61B 17/11 | 606/139 |
| 2002/0177860 A1 * | 11/2002 | Nicholas | A61B 17/11 | 606/151 |
| 2003/0014064 A1 * | 1/2003 | Blatter | A61B 17/1152 | 606/153 |
| 2009/0302089 A1 * | 12/2009 | Harari | A61B 17/115 | 227/179.1 |
| 2021/0282778 A1 | 9/2021 | Lin | | |

* cited by examiner

*Primary Examiner* — Jing Rui Ou
(74) *Attorney, Agent, or Firm* — BACON & THOMAS, PLLC

(57) ABSTRACT

A vascular anastomosis device includes a vascular jaw unit and a first vascular fastening component, wherein the vascular jaw unit is provided with a vascular anastomosis ring assembled on the first vascular fastening component. The first vascular fastening component includes a first tube provided with a first opening and a first guiding rail, a vascular positioning member connected with the first tube, a second tube arranged in the first tube, a vascular supporting unit assembled on the second tube and disposed near to the vascular positioning member, an advancing member arranged in the first tube, and a third tube arranged in the advancing member and provided with a cross rod and a guiding rod, wherein the vascular supporting unit includes a vascular supporting body and a vascular spreading member.

17 Claims, 16 Drawing Sheets

VASCULAR ANASTOMOSIS DEVICE

BACKGROUND

1. Field of the Disclosure

The present invention relates to a vascular anastomosis device.

2. Description of Related Art

Vascular anastomosis technology is a major advancement in microsurgery, which can efficiently join blood vessels, and further play a key role in microscopic repair and reconstruction. Nowadays, in addition to the traditional manual suture, other new vascular anastomosis techniques have also developed vitally, such as routine method, adhesive method, anastomotic clip method or stapler method, in which the stapler method has been proved that it can be widely used in the tissues of limbs, breasts or oral and maxillofacial parts for performing repair and reconstruction, whereby patients can obtain better treatment effects.

However, in the conventional stapler method, it still relies on manual use of vascular forceps to turn and fold the blood vessel wall outward by 90 degrees, and then fasten the turned out blood vessel wall to the staples in a specific order. However, this process relies on the skilled technique of the physician and, if the patient's blood vessels are hardened or brittle, it will be difficult to perform this process, and is likely to damage the blood vessels due to uneven three. In addition, even if this process is completed, the blood vessel wall cannot be guaranteed to be properly fixed. Therefore, the conventional method of manually operating the stapler still encounters the problems such as poor fastening effect, blood leakage from the needle hole, consumption of long time, or poor alignment, and the conventional manual method has to first treat both ends of the blood vessel wall separately for then performing vessel joining, which needs to be improved. Furthermore, because of manual fastening, it cannot ensure the same fastening effect every time the stapler is manually used, so that the fastened blood vessel may fall off in the patient's body, resulting in additional risks of surgery.

Therefore, there is an urgent need to provide an improved vascular anastomosis device to mitigate or alleviate the aforementioned problems.

SUMMARY

In view of this, according to one aspect of the present invention, a vascular anastomosis device is provided to improve the fastening effect of the vascular anastomosis device, shorten the operation time, reduce the alignment time, improve the convenience of use, perform vessel joining through simple steps, Therefore, the vascular anastomosis device may bring its function into full play, so as to reduce the burden on the surgeon, or even lower the additional risk of surgery.

Therefore, the vascular anastomosis device of the present invention includes a vascular jaw unit and a first vascular fastening component. The vascular jaw unit is provided with a vascular anastomosis ring, and the vascular anastomosis ring is sleeved on the first vascular fastening component, whereby, when the vascular anastomosis device is operated, the blood vessel may be spread outward at an angle (e.g., 90 degrees) for then being fastened on the vascular anastomosis ring.

In addition, the first vascular fastening component includes a first tube, a vascular positioning member, a second tube, a vascular supporting unit, an advancing member and a third tube. The first tube has a first end and a second end opposite to the first end, and the first tube is provided with a first opening and a first guide rail. The vascular positioning member is connected with the first end of the first tube. On the other hand, the vascular positioning member may be provided with a first protrusion at a third end opposite to the first end. A blood vessel vascular spreading member may be provided with a first concave hole arranged to correspond to the first protrusion, but the present invention is not limited thereto. By moving the first tube, the first protrusion may be moved to the outside of the first concave hole, so that the vascular positioning member may be spread outward for being sleeved on the blood vessel smoothly. Then, when the first protrusion moves to the inside of the first concave hole, the blood vessel may be attached and clamped onto the vascular supporting unit.

Next, the second tube is accommodated in the first tube. The vascular supporting unit is assembled on the second tube, and is arranged adjacent to the third end of the vascular positioning member, wherein the third end is opposite to the first end of the first tube. The vascular supporting unit includes a vascular supporting body and a vascular spreading member, and the vascular spreading member is assembled on the vascular supporting body. By moving the second tube, the vascular spreading member is pivotally rotated to spread outward the blood vessel attached to the vascular supporting unit at an angle (e.g., 90 degrees) and, at the same time, the blood vessel is fastened on the vascular anastomosis ring.

Furthermore, the advancing member is accommodated in the first tube, wherein the advancing member is arranged adjacent to the second end of the first tube. Since the advancing member is engaged in the first tube, when the advancing member moves backward, the vascular positioning member is spread outward for being sleeved on the blood vessel. The third tube is accommodated in the advancing member and is provided with a cross rod and a guiding rod, wherein the cross rod is arranged corresponding to the first opening of the first tube, so as to allow the cross rod to move within the range of the first opening of the first tube, and the guiding rod is arranged corresponding to the first guiding rail, so that the guiding rod may move along the first guiding rail.

In the vascular anastomosis device of the present invention, the vascular jaw unit includes a first portion and a second portion, and the first portion and the second portion may be pivotally connected through a pivot member. The vascular anastomosis ring may be arranged on the first portion, and another vascular anastomosis ring may be arranged on the second portion, but the present invention is not limited thereto. In addition, the present invention may further include another first vascular fastening component, wherein another vascular anastomosis ring may be sleeved on another first vascular fastening component, but the present invention is not limited thereto. After the two ends of the blood vessel are respectively fastened to the vascular anastomosis rings on the first portion and the second portion, the pivot member may be pivotally rotated to enable the first portion and the second portion to face toward each other, so that the two ends of the blood vessel can be anastomosed. On the other hand, since two sets of the same vascular anastomosis rings are provided at the same time, both ends of the blood vessel may be processed synchronously to complete the vascular anastomosis process.

In the vascular anastomosis device of the present invention, the first vascular fastening component may further include a fourth tube, wherein the fourth tube may be provided with a first through hole, and the cross rod may be assembled in the first through hole of the fourth tube and may protrude from the opening of the first tube, so as to rotate along the first through hole of the fourth tube at the same time when the third tube moves, but the present invention is not limited thereto.

The vascular anastomosis device of the present invention may further include a housing, wherein the vascular jaw unit and the first vascular fastening component may be accommodated in the housing, but the present invention is not limited thereto. In addition, the housing of the present invention may be provided with a second guiding rail, and the second guiding rail may be arranged corresponding to the cross rod, but the present invention is not limited thereto, so that the third tube may move along the path of the second guiding rail. Furthermore, the housing of the present invention may be provided with a third guiding rail, wherein a first bump may be arranged on the first tube and the third guiding rail may be arranged corresponding to the first bump, but the present invention is not limited thereto, thereby ensuring that the first tube does not rotate relative to the housing.

The vascular anastomosis device of the present invention may further include a base, which may be accommodated in the housing and may be provided with a clamping and positioning unit, wherein the vascular jaw unit may be arranged corresponding to the clamping and positioning unit, but the present invention is not limited thereto. In addition, the vascular jaw unit may include a first portion and a second portion, and the first portion and the second portion may be pivotally connected through a pivot member. The clamping and positioning unit may include a recess and, when the first portion and the second portion are clamped together, the first portion and the second portion may be accommodated in the recess. When the vascular jaw unit is forced to move, since the vascular jaw unit abuts upon the clamping and positioning unit, the pivot member starts to be rotated pivotally, so that the first portion and the second portion are clamped toward each other, thereby completing the anastomosis of blood vessel. However, the present invention is not limited thereto.

The vascular anastomosis device of the present invention may further include a first driving member, which may be arranged on the base, wherein the vascular jaw unit may be pivoted on the first driving member, but the present invention is not limited thereto. As a result, the first driving member is operatively connected with the vascular jaw unit.

In the vascular anastomosis device of the present invention, the first driving member may be provided with a third bump, and the third bump may be arranged corresponding to a first protruding portion of the base, but the present invention is not limited thereto. When the third bump is engaged with the first protruding portion, if the base moves forward, the first driving member may be driven to move forward at the same time; however, the first driving member may only move forward relative to the base, but not moves backward relative to the base.

The vascular anastomosis device of the present invention may further include a second driving member, which may be assembled in a sliding slot of the advancing member and may be provided with a first connecting member, wherein the first connecting member may be connected with a first linkage element, but the present invention is not limited thereto. When the first linkage element moves, the second driving member may be driven to move, and the sliding slot provides an appropriate moving space for the second driving member.

The vascular anastomosis device of the present invention may further include a third driving member, which is further provided with a second protrusion. The second protrusion may be arranged corresponding to a sliding member, and the sliding member may be pivoted with a rotation element, wherein the rotation element may be arranged adjacent to a first fastening member of the housing, the rotation element may be arranged corresponding to a second bump of the housing, and the rotation element may be arranged corresponding to a fourth bump of the advancing member, but the present invention is not limited thereto. In addition, the present invention may further include a device body, wherein the housing may include a first fastening member and may be assembled into the device body through the first fastening member, but the present invention is not limited thereto. When the rotation element rotates due to being in contact with a second bump of the housing, the rotation element may be engaged with the fourth bump, so that the rotation element may be operatively connected with the advancing member.

The vascular anastomosis device of the present invention may further include a fifth tube, which may be accommodated in the device body, wherein the fifth tube member may be provided with an engaging member and an elastic element, but the present invention is not linked thereto. In addition, the present invention may farther include a displacement control member, which may be accommodated in the device body, wherein the displacement control member may be arranged corresponding to the engaging member, but the present invention is not limited thereto. When the engaging member is in contact with the displacement control member, the engaging member starts to rotate and a tenon of the engaging member is released, so that the advancing member and the fifth tube may move relatively.

Other objects, advantages, and novel features of the disclosure will become more apparent from the following detailed description when taken in conjunction with the accompanying drawings.

DETAILED DESCRIPTION

Various embodiments of the present invention are provided below. These embodiments are provided to illustrate the technical content of the present invention, but not to limit the scope of the claim of the present invention. A feature of one embodiment may be applied to other embodiments by suitable modification, substitution, combination or separation.

It should be noted that, in this text, unless otherwise specified, having "a" component is not limited to having a single component, but may have one or more components.

In addition, in this text, unless otherwise specified, ordinal numbers such as "first" and "second" are only used to distinguish multiple components with the same name, and do not mean that there is a rank, hierarchy, execution sequence, or process sequence between them. A "first" component and a "second" component may appear together in the same member or separately in different members. The presence of a component with a higher ordinal number does not necessarily imply the presence of another component with a lower ordinal number.

In addition, in this text, the terms, such as "upper", "lower", "left", "right", "front", "rear" and "between", are only used to describe the relative position among a plurality of components, and may be extended to include translation, rotation, or mirroring in interpretation.

In addition, in this text, unless otherwise specified, "a component is on another component" or the like does not necessarily mean that the component is in contact with the other component.

In addition, in this text, the term "preferred" or "more preferred" is used to describe optional or additional components or features; that is, those components or features are not required and may be omitted.

In addition, in this text, unless otherwise specified, the expression of one component "suitable for" or "applicable to" another component means that said another element is not part of the subject matter of the application, but is an exemplary ground or reference that helps to envisage the nature or application of the element. Similarly, in this text, unless otherwise specified, the expression of a component "suitable for" or "applicable to" a configuration or an action describes the feature of the component, but not that the configuration has been set or the action has been performed.

Structure of First Vascular Fastening Component 20

Figure 1:
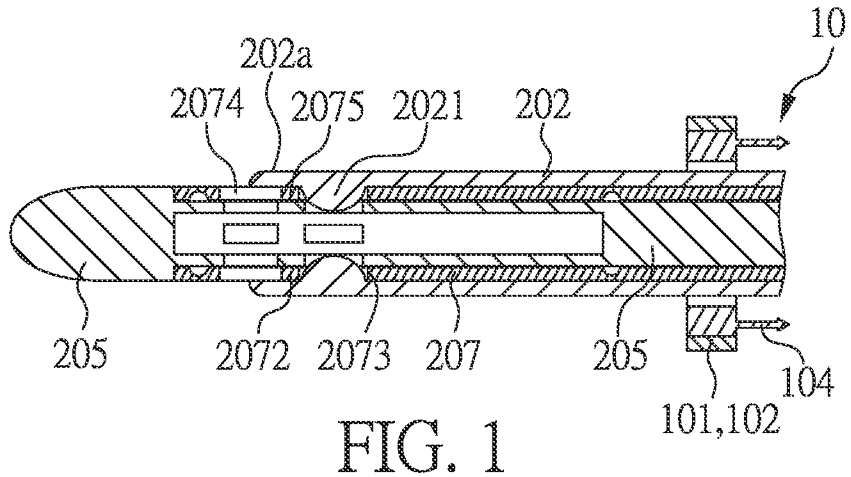
FIGS. 1 to 6 are schematic diagrams illustrating the actuating mechanism of the vascular jaw unit and part of the first vascular fastening component according to an embodiment of the present invention.

FIG. 1 is a cross-sectional view of the vascular jaw unit 10 and part of the first vascular fastening component 20 according to an embodiment of the present invention.

Figure 7:
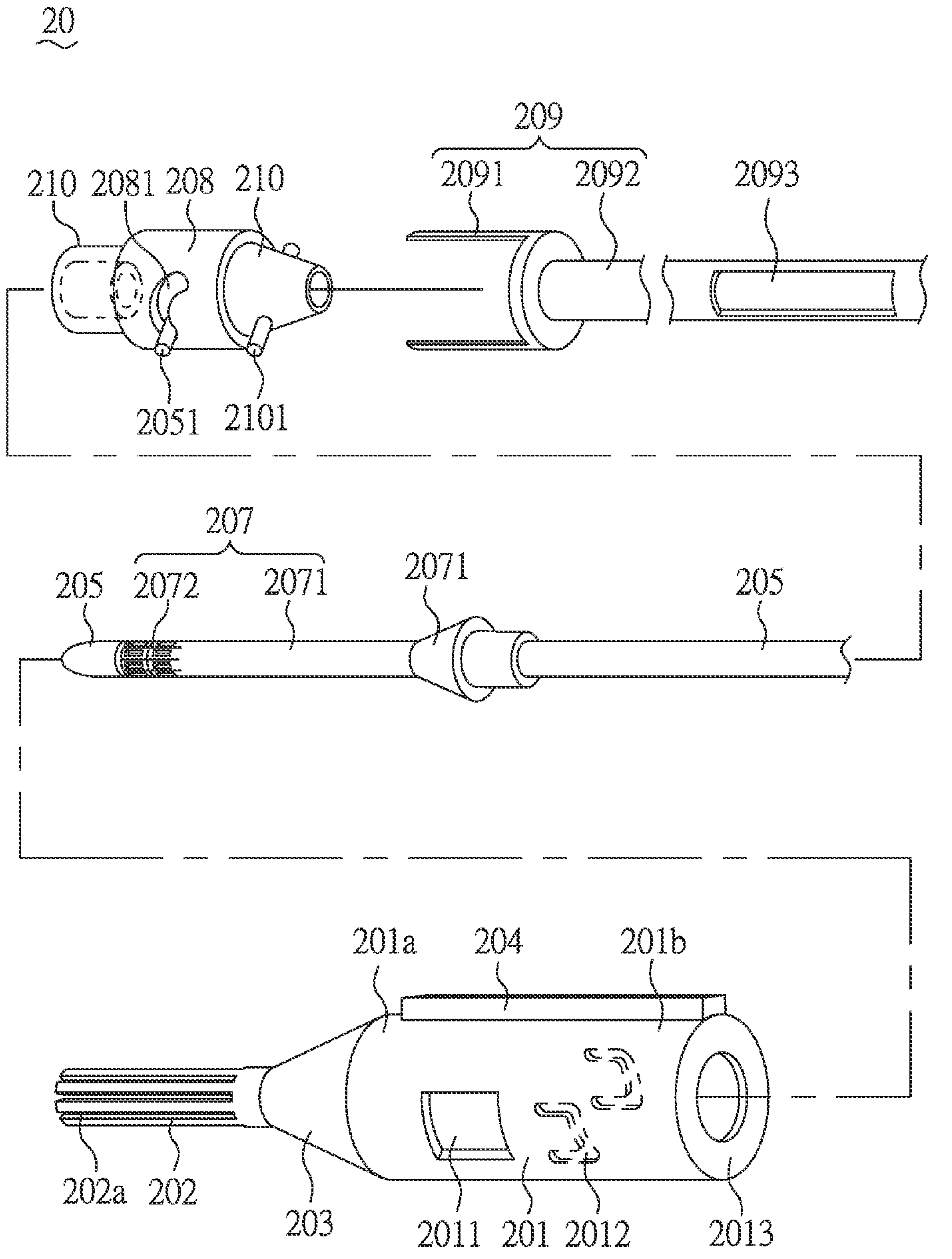
FIG. 7 is an exploded view of the first vascular fastening component according to an embodiment of the present invention.

FIG. 7 is an exploded view of the first vascular fastening component 20 according to an embodiment of the present invention.

Figure 8:
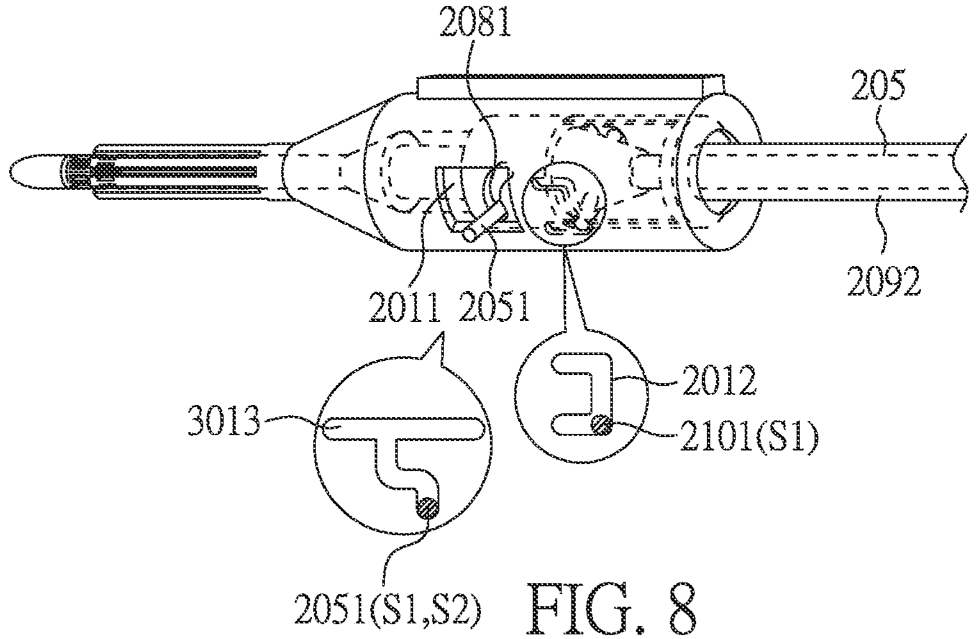
FIGS. 8 to 11 are schematic diagrams illustrating the actuating mechanism of the first vascular fastening component according to an embodiment of the present invention.

FIG. 8 is a perspective view of the first vascular fastening component 20 according to an embodiment of the present invention.

Figure 12:
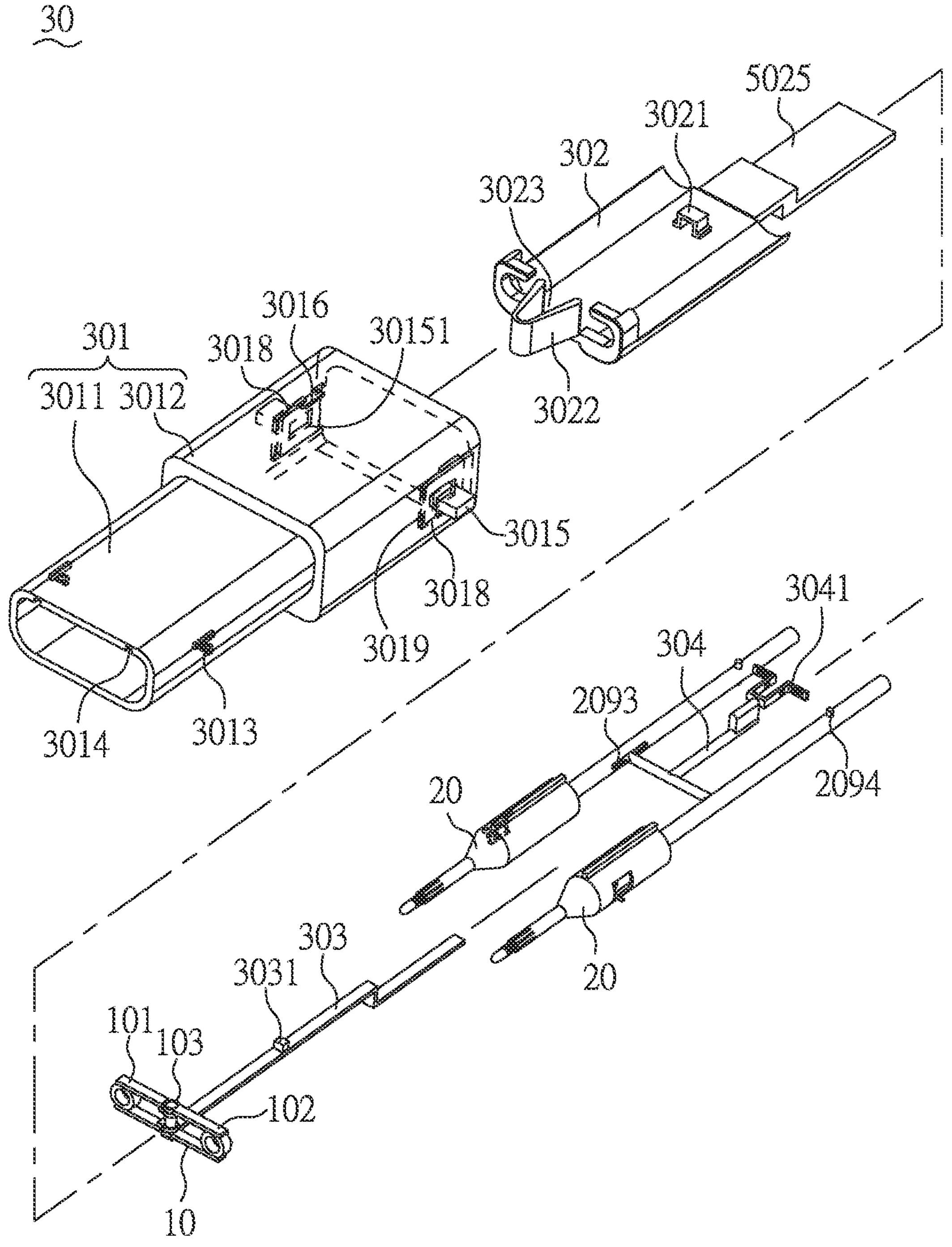
FIG. 12 is an exploded view of the vascular anastomosis assembly according to an embodiment of the present invention.

As shown in FIG. 1, FIG. 7 and FIG. 8, the first vascular fastening component 20 of this embodiment includes a first tube 201, a vascular positioning member 202, a first joining member 203, a first bump 204, a second tube 205, a vascular supporting unit 207, a fourth tube 208, an advancing member 209 and a third tube 210. The first tube 201 is connected to the vascular positioning member 202 through the first joining member 203; in other words, the first joining member 203 is arranged between the first tube 201 and the vascular positioning member 202. The first tube 201 has a first end 201*a* and a second end 201*b* opposite to the first end 201*a*, and the first tube 201 is provided with a first opening 2011 and a first guiding rail 2012. The vascular positioning member 202 is provided with a first protrusion 2021 on the inner side of the third end 202*a* corresponding to the first end 201*a* of the first tubular member 201. On the other hand, the first bump 204 is arranged on the first tube 201, and corresponds to the third guiding rail 3014 of the housing 301 (as shown in FIG. 12).

In addition, the second tube 205 is accommodated in the first tube 201. The vascular supporting unit 207 is sleeved outside the second tube 205 and arranged adjacent to the third end 202*a* of the vascular positioning member 202. The vascular supporting unit 207 includes a vascular supporting body 2071 and a vascular spreading member 2072. The vascular spreading member 2072 is assembled on the vascular supporting body 2071, and the vascular spreading member 2072 is provided with a first concave hole 2073, a second concave hole 2074 and a rotation shaft 2075, wherein the first concave hole 2073 is arranged corresponding to the first protrusion 2021. In this embodiment, the vascular supporting unit 207 is accommodated. In the vascular positioning member 202 and the first joining member 203, and is sleeved outside the second tube 205.

Furthermore, the advancing member 209 is accommodated in the first tube 201 and sleeved outside the second tuber 205, and the advancing member 209 is arranged adjacent to the second end 201*b* of the first tube 201. In this embodiment, the advancing member 209 includes a front advancing portion 2091 and a rear advancing portion 2092, and a sliding slot 2093 is provided on the rear advancing portion. 2092. On the other hand, the third tube 210 is accommodated in the front advancing portion 2091 of the advancing member 209 and provided with a guiding rod 2101 and a cross rod 2051, and the fourth tube 208 is sleeved outside the third tube 210, wherein the guiding rod 2101 is arranged corresponding to the first guiding rail 2012 of the first tube 201. That is, the guiding rod 2101 may move along the first guiding rail 2012, and the cross rod 2051 is assembled in the first through hole 2081 of the fourth tube 208 and protrudes from the first opening 2011 of the first tube 201.

Structure of Vascular Anastomosis Assembly 30

FIG. 12 is an exploded view of the vascular anastomosis assembly 30 according to an embodiment of the present invention.

Figure 13:
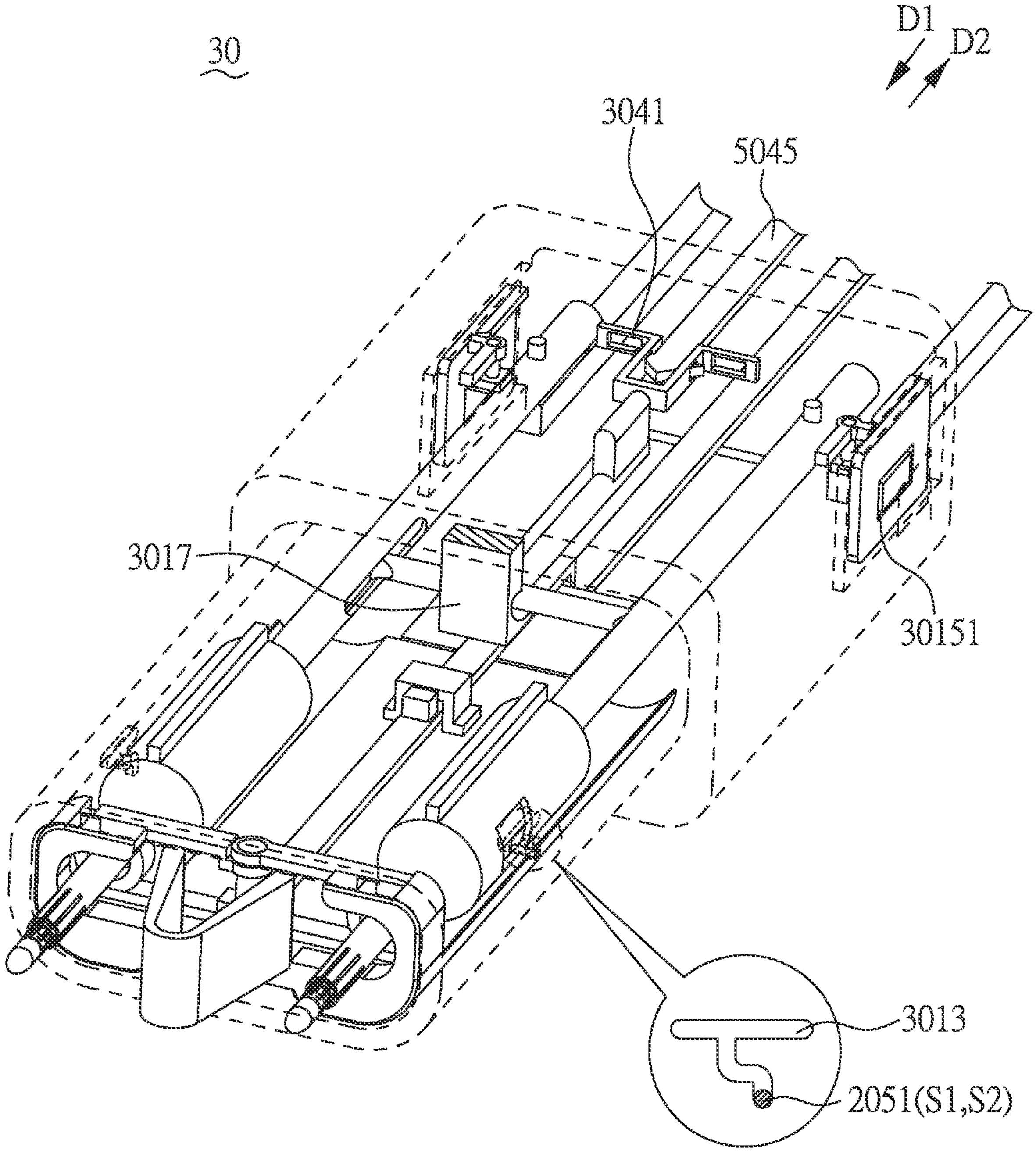
FIGS. 13 to 17 are schematic diagrams illustrating the actuating mechanism of the vascular anastomosis assembly according to an embodiment of the present invention.

FIG. 13 is a perspective view of the vascular anastomosis assembly 30 according to an embodiment of the present invention.

As shown in FIG. 1, FIG. 12 and FIG. 13, the vascular anastomosis assembly 30 of this embodiment includes a vascular jaw unit 10, a vascular fastening component 20, a housing 301, a base 302, a first driving member 303 and a second driving member 304. The vascular jaw unit 10 includes a first portion 101 and a second portion 102, and the first portion 101 and the second portion 102 are pivotally connected through a pivot member 103. In addition, the vascular jaw unit 10 is provided with a vascular anastomosis ring 104, and the vascular anastomosis ring 104 is sleeved on the first vascular fastening component 20. In this embodiment, the vascular anastomosis assembly 30 has two vascular anastomosis rings 104 and two first vascular fastening components 20. The vascular anastomosis ring 104 is arranged on the first portion 102 and sleeved on the first vascular fastening component 20, and the other vascular anastomosis ring 104 is arranged on the second portion 102 and sleeved on the other first vascular fastening component 20. In addition, the first vascular fastening component 20 is inserted in the first portion 101, and the other first vascular fastening component 20 is inserted in the second portion 102.

Next, the vascular jaw unit 10, the first vascular fastening component 20, the base 302, the first driving member 303 and the second driving member 304 are accommodated in the housing 301, and the housing 301 includes a front housing portion 3011 and a rear housing portion 3012. Inside the housing 301, there are two second guide rails 3013, two third guide rails 3014, two first fastening members 3015, two sliding members 3018 and two grooves 3019 correspondingly arranged, and a single fifth bump 3017. The second guiding rail 3013 is arranged corresponding to the cross rod 2051 (as shown in FIG. 7), and the third guiding rail 3014 is arranged corresponding to the first hump 204 on the first tube 201 (as shown in FIG. 7), while the fifth bump 3017 is provided to block the second driving member 304 so that the second driving member 304 cannot move along the direction D1. On the other hand, the base 302 is provided with a first protruding portion 3021 and a clamping and positioning unit 3022, and the clamping and positioning unit 3022 has a recess 3023, wherein the vascular jaw unit 10 and the clamping and positioning unit 3022 are correspondingly arranged. In addition, the groove 3019 accommodates a sliding member 3018, and the sliding member 3018 may move in the groove 3019 along the direction D1 or the direction D2.

In this embodiment, the first driving member 303 is arranged on the base 302, wherein the vascular jaw unit 10 is pivoted on the first driving member 303. In more detail, the first driving member 303 is pivotally connected with the pivot member 103 of the vascular jaw unit 10. In addition, the first driving member 303 is provided with a third bump 3031, and the third bump 3031 is arranged corresponding to the first protruding portion 3021 of the base 302. The second driving member 304 is assembled in the sliding slot 2093 of the advancing member 209 to be connected to the second tube 205, and is provided with a first connecting member 3041 (as shown in FIG. 7), wherein the first connecting member 3041 is connected with the first linkage element 5045.

Structure of Vascular Anastomosis Device 1

Figure 18:
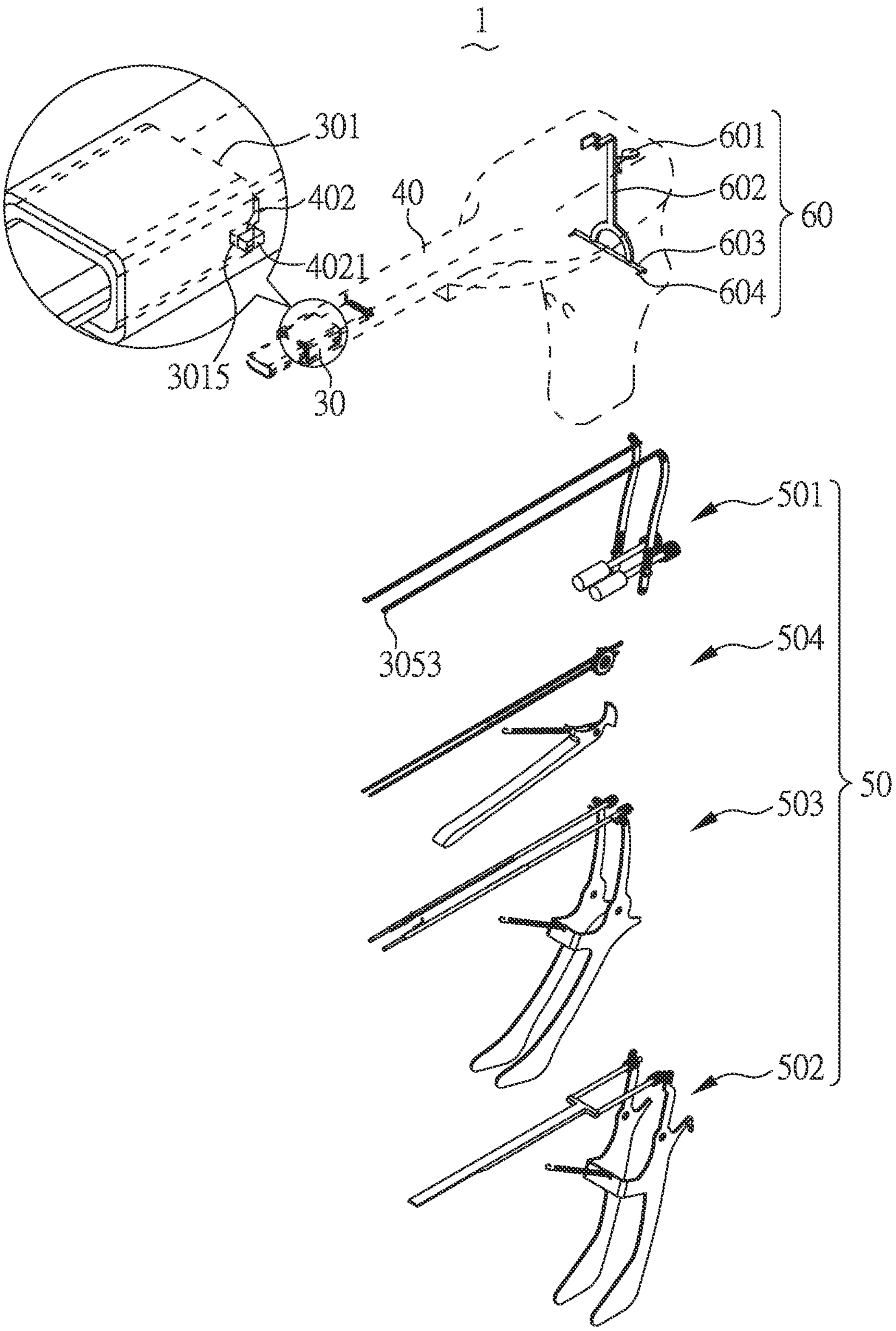
FIG. 18 is a perspective view of the vascular anastomosis device according to an embodiment of the present invention.

FIG. 18 is a perspective view of the vascular anastomosis device 1 according to an embodiment of the present invention.

Figure 19:
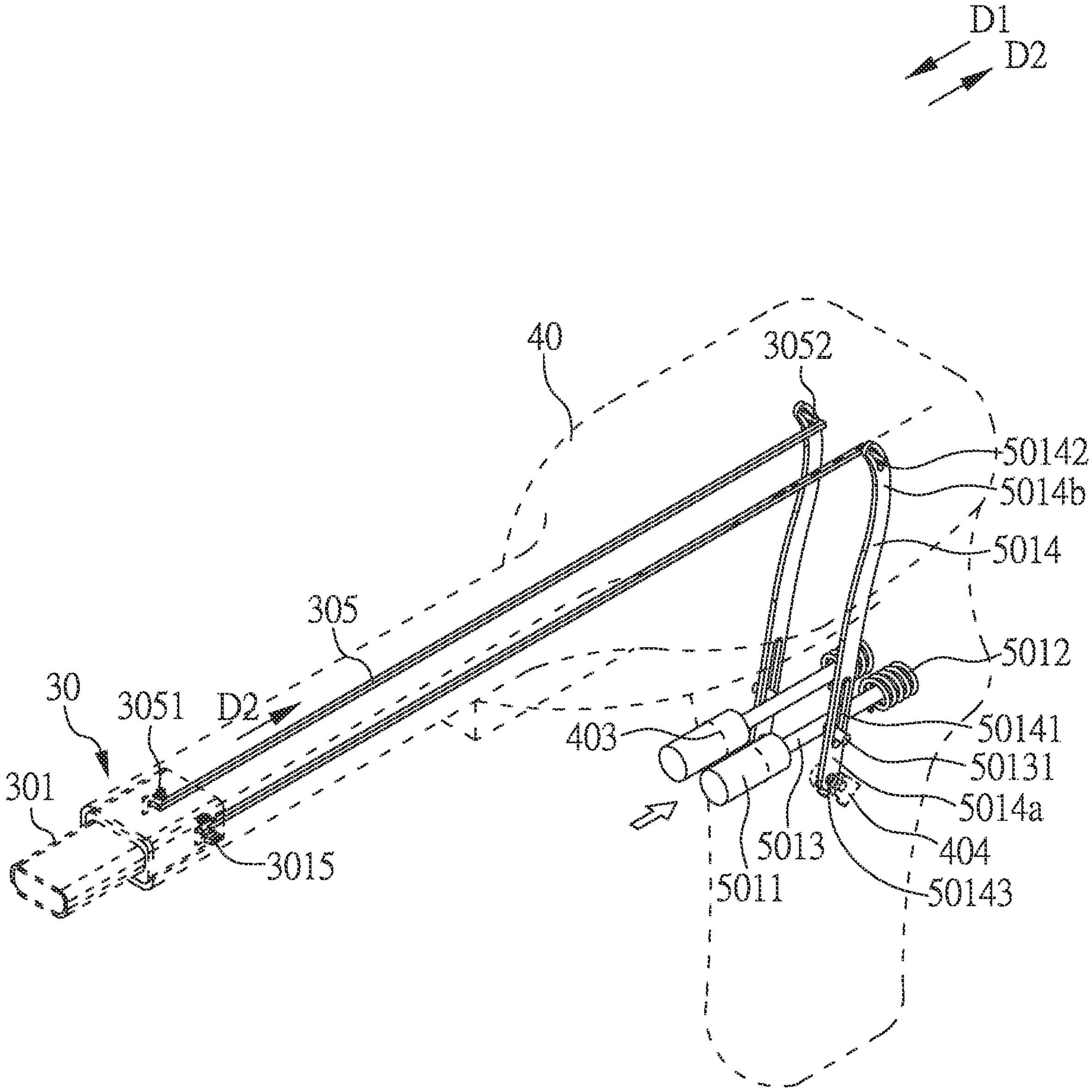
FIG. 19 is a perspective view of the first operating unit according to an embodiment of the present invention.

FIG. 19 is a perspective view of the first operating unit 501 according to an embodiment of the present invention.

Figure 20:
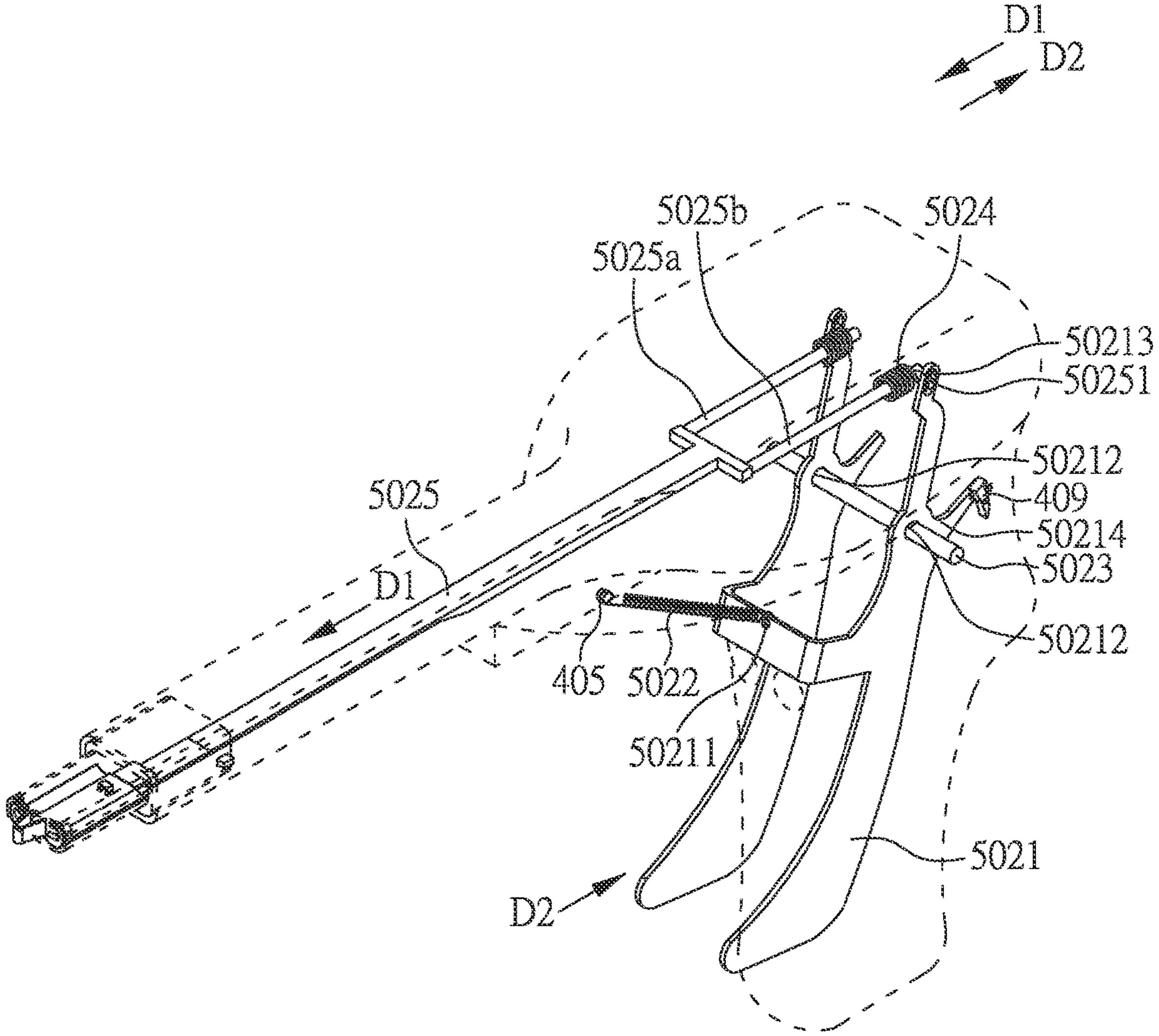
FIG. 20 is a perspective view of the second operating unit according to an embodiment of the present invention.

FIG. 20 is a perspective view of the second operating unit 502 according to an embodiment of the present invention.

Figure 21:
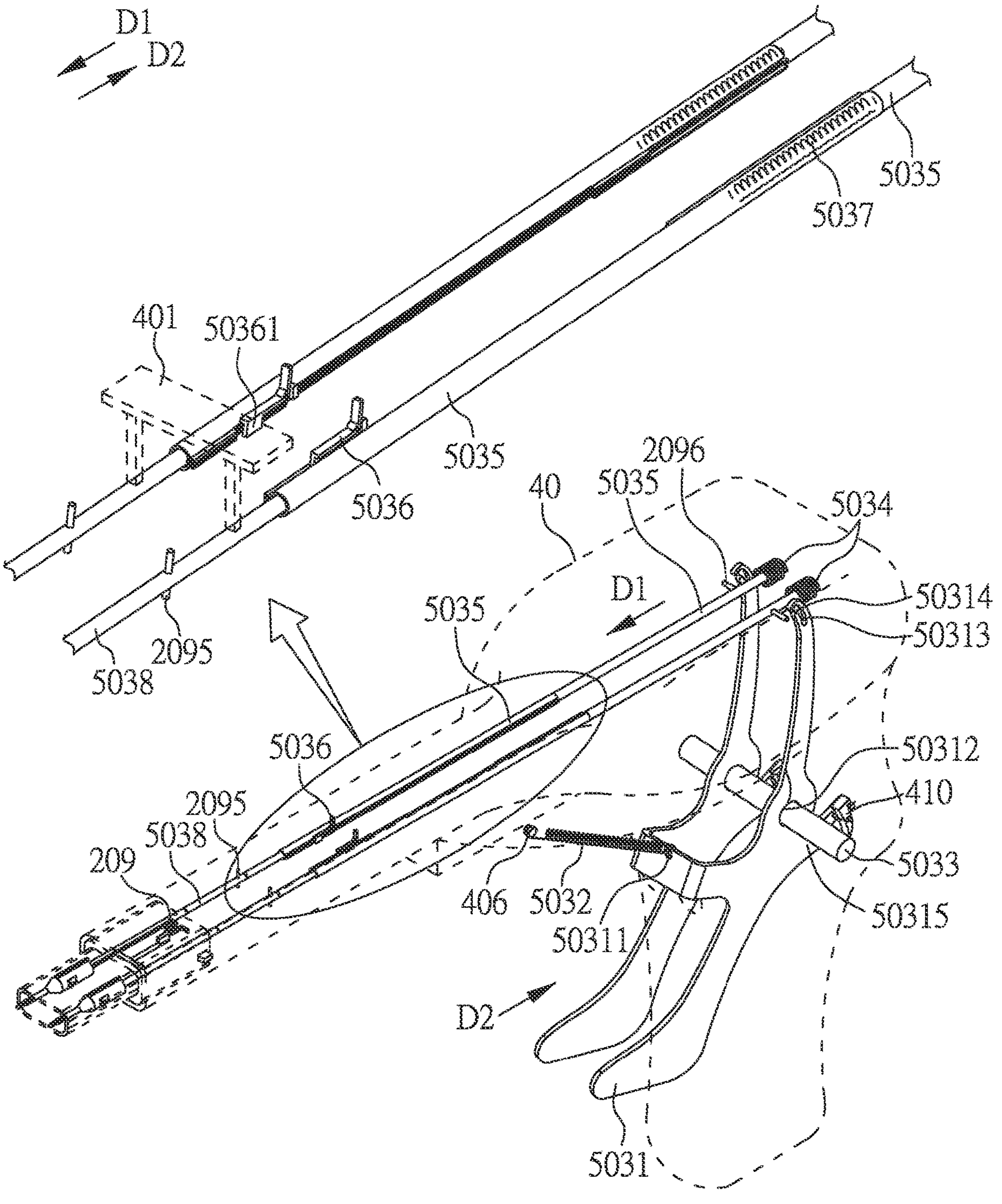
FIG. 21 is a perspective view of the third operating unit according to an embodiment of the present invention.

FIG. 21 is a perspective view of the third operating unit 503 according to an embodiment of the present invention.

Figure 22:
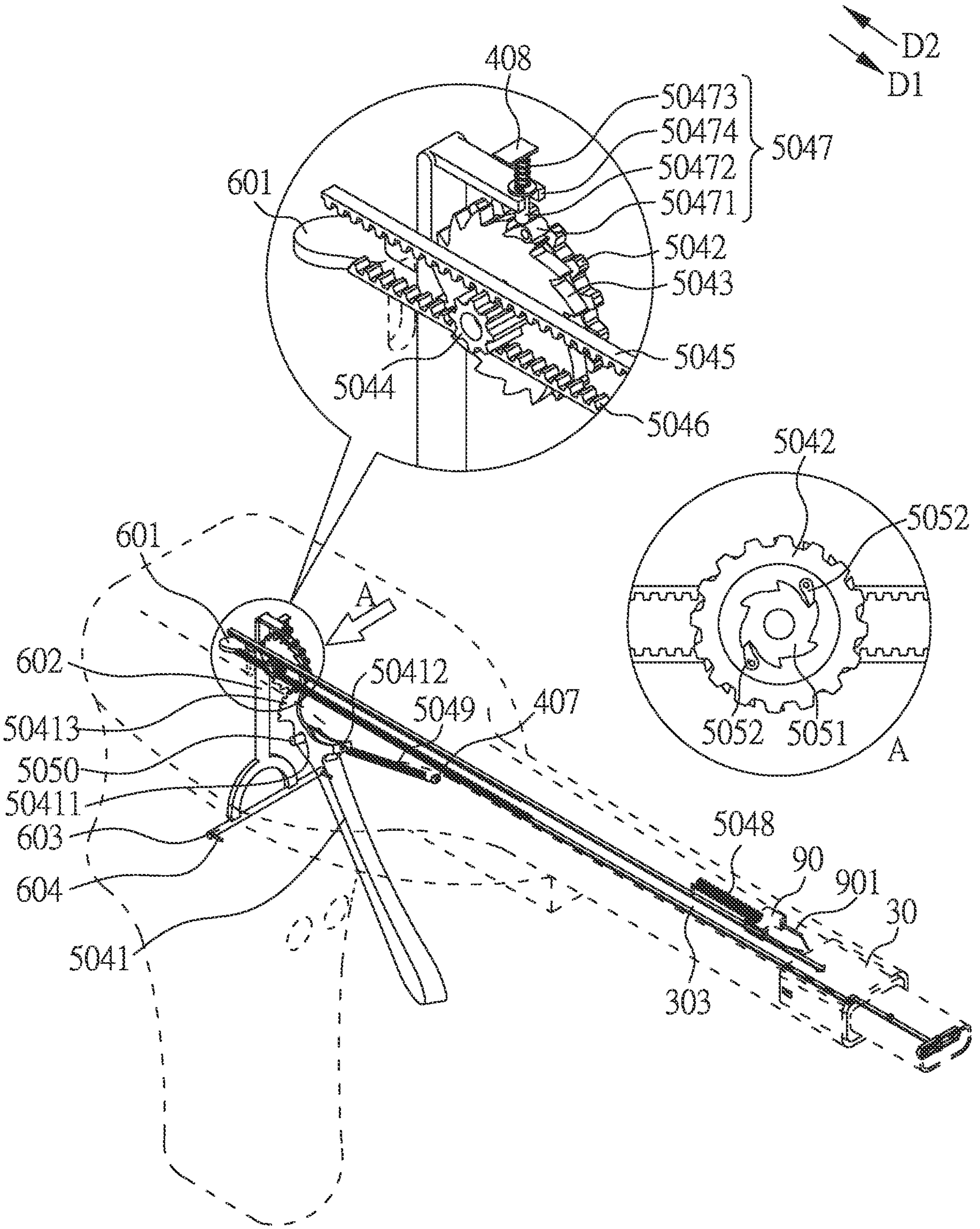
FIG. 22 is a perspective view of the fourth operating unit according to an embodiment of the present invention.

FIG. 22 is a perspective view of the fourth operating unit 504 according to an embodiment of the present invention, As shown in FIG. 18, the vascular anastomosis device 1 of this embodiment includes a vascular anastomosis assembly 30, a device body 40, an operating assembly 50 and a release assembly 60, wherein the device body 40 accommodates the vascular anastomosis assembly 30, an operating assembly 50 and the release assembly 60. The structure of the vascular anastomosis assembly 30 can be known from the aforementioned description. The device body 40 has two correspondingly arranged second openings 402 (due to the viewing angle, only one second opening 402 is shown in FIG. 18), and the second opening 402 is provided with a third button 4021 arranged corresponding to the first fastening member 3015 of the housing 301. The housing 301 is assembled to the second opening 402 of the device body 40 through the first fastening member 3015, so that the vascular anastomosis assembly 30 is accommodated in the device body 40. In addition, by pressing the third button 4021 to drive the first fastening member 3015 to push away the second protrusion 3053 of the third driving member 305 away, the vascular anastomosis assembly 30 may be separated from the device body 40 (as shown in FIG. 19).

Figure 3:
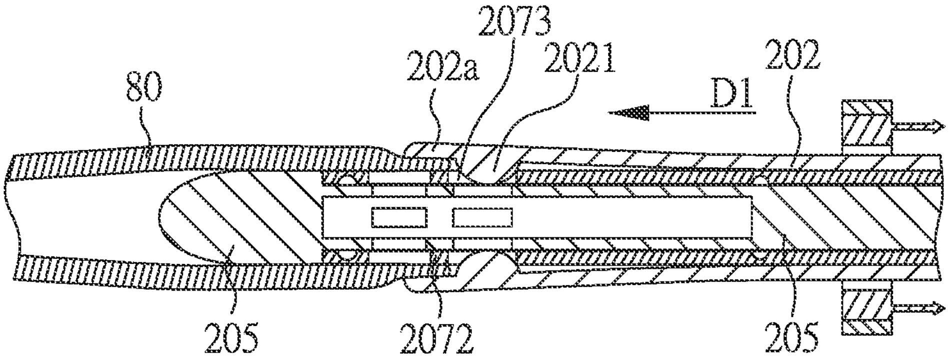

As shown FIG. 18 and FIG. 19, the operating assembly 50 includes a first operating unit 501, a second operating unit 502, a third operating unit 503 and a fourth operating unit 504, wherein the first operating unit 501 includes two first buttons 5011, two first elastic elements 5012, two first linking rods 5013, two second linking rods 5014 and two third driving members 305. In this embodiment, the first button 5011 is arranged corresponding to the third opening 403 of the device body 40, so that part of the first button 5011 is accommodated in the device body 40. The first button 5011 is connected with the first elastic element 5012 through the first linking rod 5013, and the first linking rod 5013 is provided with a third fastening member 50131, which is assembled to the second through hole 50141 of the second linking rod 5014 adjacent to the first terminal 5014*a*. On the other hand, the third driving member 305 has a fourth fastening member 3052, and the fourth fastening member 3052 is assembled to the third through hole 50142 of the second linking rod 5014 adjacent to the second terminal 5014*b*. In addition, the second linking rod 5014 of the first operating unit 501 is further provided with a fourth through hole 50143 adjacent to the first terminal 5014*a*, so that the first operating unit 501 is pivoted to the first fastening base 404 in the device body 40 through the fourth through hole 50143. In another embodiment of the present invention, the two first buttons 5011 of the first operating unit 501 may be respectively operated to sequentially clamp two blood vessels 80 (as shown in FIG. 3), Furthermore, please refer to FIG. 12, FIG. 14 and FIG. 18. In this embodiment, the front end of each third driving member 305 is provided with a second protrusion 3053. The second protrusion 3053 is engaged with the fourth opening 30151 on the sliding member 3018, and the sliding member 3018 is pivoted with a rotation element 3051, wherein the rotation elements 3051 are respectively arranged adjacent to the first fastening members 3015 of the housing 301, the rotation element 3051 is arranged corresponding to the second bump 3016 of the housing 301, and the rotation element 3051 is arranged corresponding to the fourth bump 2094 of the advancing member 209. On the other hand, please refer to FIG. 12 and FIG. 14, since the second protrusion 3053 is engaged with the fourth opening 30151 on the sliding member 3018, the third button 4021 may be pressed to drive the first fastening member 3015, so that the second protrusion 3053 is separated from the fourth opening 30151, thereby separating the vascular anastomosis assembly 30 from the device body 40. Therefore, the vascular anastomosis assembly 30 is a detachable assembly (as shown in FIG. 12).

In addition, as shown in FIG. 18 and FIG. 20, the second operating unit 502 includes a second holding element 5021, a second elastic element 5022, a fifth fastening member 5023, two third elastic elements 5024 and a fourth driving member 5025. The second holding element 5021 has a fifth through hole 50211, two sixth through holes 50212, two seventh through holes 50213 and two second protruding portions 50214. In this embodiment, both ends of the second elastic element 5022 are respectively fastened to the fifth through hole 50211 and the second fastening base 405 of the device body 40. On the other hand, by the fifth fastening member 5023 passing through the two sixth through holes 50212 arranged correspondingly, and taking the fifth fastening member 5023 as a pivot axis, the second holding element 5021 is pivoted in the device body 40. The fourth driving member 5025 has a first part 5025*a* and a second part 5025*b*, wherein the first part 5025*a* and the second part 5025*b* are respectively connected with two different third elastic elements 5024, and the first part 5025*a* and the second part 5025*b* are each provided with a sixth fastening member 50251, which is assembled to the seventh through hole 50213 of the second holding element 5021. In addition, when the second holding element 5021 is pressed to the utmost, the two second protruding portions 50214 of the second holding element 5021 may be respectively fastened to the seventh fastening bases 409 of the device body 40, and fastened on the fourth linking rod 603 of the release member 60. In another embodiment of the present invention, the two second holding elements 5021 of the second operating unit 502 may be integrated into one body to form a single holding element, so as to improve the convenience of operation.

Furthermore, as shown in FIG. 18 and FIG. 21, the third operating unit 503 includes a third holding element 5031, a fourth elastic element 5032, a seventh fastening member 5033, two fifth elastic elements 5034, two fifth tubes 5035, two engaging members 5036 and two sixth elastic elements 5037. The third holding element 5031 has an eighth through hole 50311, two ninth through holes 50312, two tenth through holes 50313, and two third protruding portions 50315, wherein both ends of the fourth elastic element 5032 are respectively fastened to the eighth through hole 50311 and the third fastening base 406 of the device body 40. In addition, by the seventh fastening member 5033 passing through the two ninth through holes 50312 on the third holding element 5031, and taking the seventh fastening member 5033 as a pivot axis, the third holding element 5031 is pivoted in the device body 40, On the other hand, the fifth tube 5035 and the sixth elastic element 5037 are accommodated in the device body 40, and the fifth tube 5035 is sleeved outside the sixth tube 5038. In this embodiment, the fifth tube 5035 is connected to the sixth tube 5038 through the sixth elastic element 5037, and the fifth tube 5035 is also connected to the fifth elastic element 5034. Furthermore, the fifth tube 5035 is provided with an eighth fastening member 2096, and the eighth fastening member 2096 may be assembled in the tenth through hole 50313 of the third holding element 5031 through the fourth opening 50314. Next, the engaging member 5036 has a tenon 50361, and the engaging member 5036 is arranged on the fifth tube 5035, while the tenon 50361 is arranged corresponding to the displacement control member 401 of the device body 40. When the third holding element 5031 is pressed to the utmost, the two third protruding portions 50315 of the third holding element 5031 may be respectively fastened to the eighth fastening bases 410 of the device body 40 and fastened on the fourth linking rod 603 of the release assembly 60. In another embodiment of the present invention, the two third holding elements 5031 of the third operating unit 503 may be integrated into one body to form a single holding element, so as to improve the convenience of operation.

As shown in FIG. 18 and FIG. 22, the fourth operating unit 504 includes a fourth holding element 5041, a first gear 5042, a second gear 5043, a third gear 5044, a first linkage element 5045, a second linkage element 5046, a locking assembly 5047, a seventh elastic element 5048, an eighth elastic element 5049, a ninth fastening member 5050, a fourth gear 5051 and a second locking element 5052. The fourth holding element 5041 has an eleventh through hole 50411 and a twelfth through hole 50412, and both ends of the eighth elastic element 5049 are respectively fastened to the twelfth through hole 50412 and the fourth fastening base 407 of the device body 40. On the other hand, by the ninth fastening member 5050 passing through the eleventh through hole 50411 on the fourth holding member 5041, and taking the ninth fastening member 5050 as a pivot axis, the fourth holding element 5041 is pivoted in the device body 40. In addition, the fourth holding element 5041 is provided with a toothed structure 50413, and the toothed structure 50413 meshes with the first gear 5042. In this embodiment, the first gear 5042, the second gear 5043, the third gear 5044 and the fourth gear 5051 are arranged concentrically, while the first linkage element 5045 and the second linkage element 5046 mesh with the third gear 5044, the first linkage element 5045 is connected with the first connecting member 3041, the second linkage element 5046 is connected with the first driving member 303 (as shown in FIG. 12), and the first linkage element 5045 is further connected with the control assembly 90 through the seventh elastic element 5048. In addition, the control assembly 90 includes a control unit 901 and, when the fourth holding element 5041 is pressed to the utmost, the first linkage element 5045 moves along the direction D2, so that the first connecting member 3041 contacts the control unit 901, thereby allowing the first linkage element 5045 to be released from the first connecting member 3041 so as to facilitate subsequent operations (as shown in FIG. 13). On the other hand, the fourth gear 5051 is arranged inside the hollow first gear 5042 and meshes with the two second locking elements 5052, respectively.

Next, as shown in FIG. 18 and FIG. 22, the locking assembly 5047 includes a first locking element 50471, an adjustment element 50472, a ninth elastic element 50473 and a fifth fastening base 50474, wherein the first locking element 50471 meshes with the second gear 5043, the adjustment element 50472 is connected with the ninth elastic element 50473 and abuts upon the first locking element 50471, and the ninth elastic element 50473 is fastened to the sixth fastening base 408 of the device body 40. On the other hand, the fifth fastening base 50474 of the locking assembly 5047 is assembled on the third linking rod 602 of the release assembly 60, and the third linking rod 602 is provided with a second button 601 and is connected with the fourth linking rod 603. In addition, the fourth linking rod 603 is provided with a tenth fastening member 604, and the tenth fastening member 604 is pivoted in the device body 40.

Actuating Mechanism of Vascular Jaw Unit 10 and First Vascular Fastening Component 20

FIGS. 1 to 6 are schematic diagrams illustrating the actuating mechanism of the vascular jaw unit 10 and part of the first vascular fastening component 20 (as shown in FIG. 7) according to an embodiment of the present invention.

As shown in FIG. 1, in which the vascular jaw unit 10 and the first vascular fastening component 20 (as shown in FIG. 7) are not actuated at this moment, the first protrusion 2021 of the vascular positioning member 202 is arranged inside the first concave hole 2073 of the vascular spreading member 2072, and the first portion 101 or the second portion 102 of the vascular jaw unit 10 is sleeved outside the vascular positioning member 202.

Figure 2:
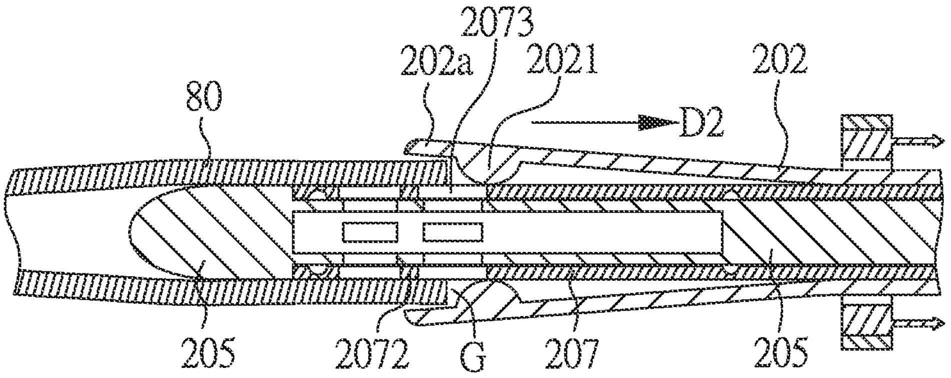

As shown in FIG. 2, at this moment, it is in the state of being inserted into the blood vessel 80. By operating the first button 5011 of the first operating unit 501, wherein the actuating mechanism of the first operating unit 501 will be described in detail below (as illustrated in FIG. 18 and FIG. 19), the vascular positioning member 202 moves along the direction D2, and the first protrusion 2021 of the vascular positioning member 202 is separated from the first concave hole 2073 of the vascular spreading member 2072, thereby causing the vascular positioning member 202 to be slightly spread outward to form a gap G between the third end 202*a* of the vascular positioning member 202 and the vascular supporting body 2071, so that the blood vessel 80 may be sleeved on the vascular supporting body 2071 and accommodated in the gap G.

As shown in FIG. 3, at this moment, it is the state in which the blood vessel 80 has been sleeved on the vascular supporting body 2071. By operating the first operating unit 501 (as shown in FIG. 18), the vascular positioning member 202 moves along the direction D1. The first protrusion 2021 of the vascular positioning member 202 returns to the first concave hole 2073 of the vascular spreading member 2072, so that the gap G disappears (as shown in FIG. 2), and the third end 202*a* of the vascular positioning member 202 may clamp the blood vessel 80.

Figure 4:
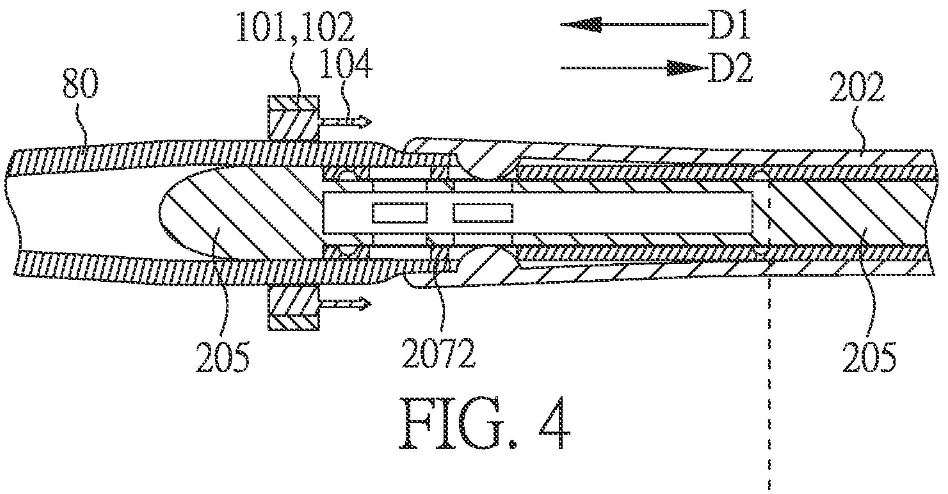

As shown in FIG. 4, as well as FIG. 12, at this moment, it is the state in which the vascular jaw unit 10 is actuated. By operating the second operating unit 502, wherein the actuating mechanism of the second operating unit 502 will be described in detail below (as shown in FIG. 18), the vascular jaw unit 10 moves along the direction D1 from the position that it is originally sleeved outside the vascular positioning member 202 (as shown in FIG. 3) to the position that it is sleeved outside the blood vessel 80, so as to facilitate the subsequent process of fastening the blood vessel to the vascular anastomosis ring 104.

Figure 5:
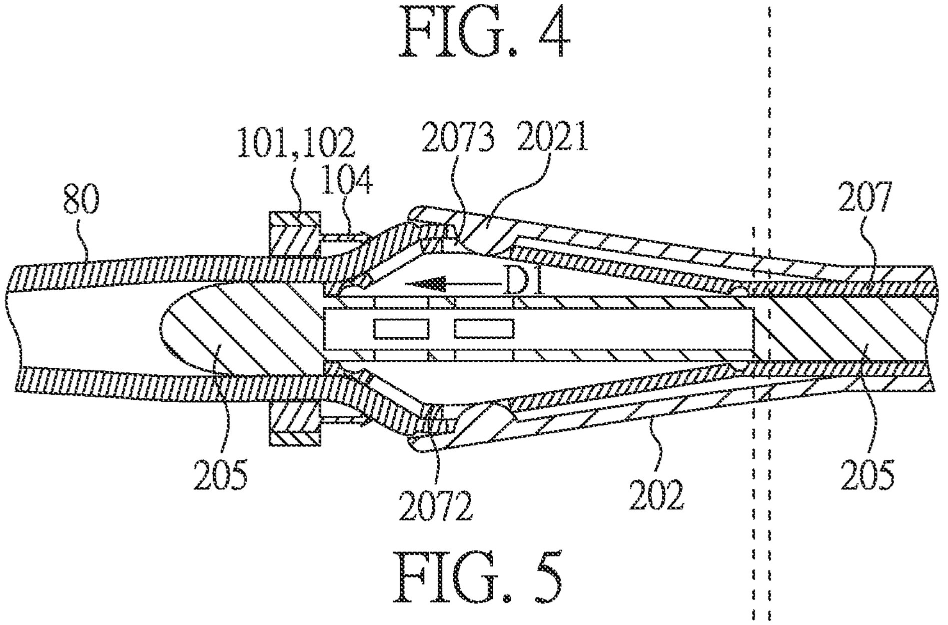
Figure 6:
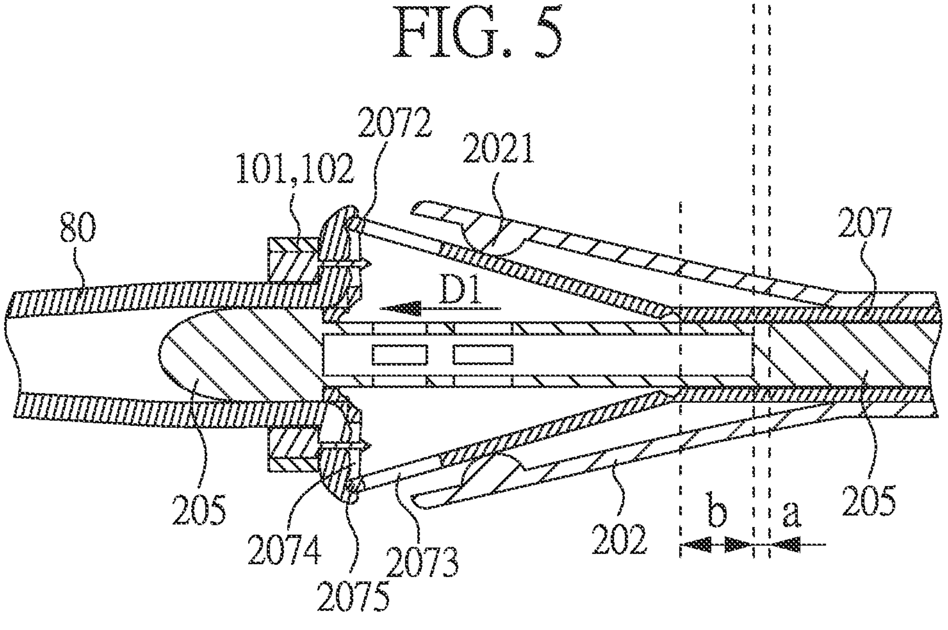

As shown in FIG. 5, as well as FIGS. 6 to 7, at this moment, the blood vessel 80 is in the state of being spread outward. By operating the third operating unit 503, wherein the actuating mechanism of the third operating unit 503 will be described in detail below (as shown in FIG. 18), the vascular spreading member 2072 operatively connected with the third tube 210 moves along the direction D1. Since the vascular spreading member 2072 is assembled on the vascular supporting body 2071, the vascular spreading member 2072 may be spread outward after being pivotally rotated, so that the blood vessel 80 attached to the vascular spreading member 2072 may be spread outward. In addition, since the vascular spreading member 2072 and the vascular positioning member 202 synchronously move along the direction D1 by a distance "a", the first protrusion 2021 is still engaged with the first concave hole 2073 to firmly clamp the blood vessel 80.

As shown in FIG. 6, as well as FIG. 1, at this moment, the blood vessel 80 is in the state of being fastened to the vascular anastomosis ring 104. By continuously operating the third operating unit 503 (as shown in FIG. 18), the vascular spreading member 2072 is pivotally rotated through the rotation shaft 2075, and moves along the direction D1 by a distance "b" to fasten the blood vessel 80 on the vascular anastomosis ring member 104 so as to complete the step of blood vessel anastomosis.

Actuating Mechanism of First Vascular Fastening Component 20

FIGS. 8 to 11 are schematic diagrams illustrating the actuating mechanism of the first vascular fastening component 20 (as shown in FIG. 7) according to an embodiment of the present invention.

As shown in FIG. 8, at this moment, the first vascular fastening component 20 is in the state of not being actuated (as shown in FIG. 7), which corresponds to FIG. 1. The guiding rod 2101 is assembled in the first guiding rail 2012, and the cross rod 2051 is assembled in the first through hole 2081 and protrudes from the first opening 2011, wherein the guiding rod 2101 and the cross rod 2051 are disposed at the first position S1.

Figure 9:
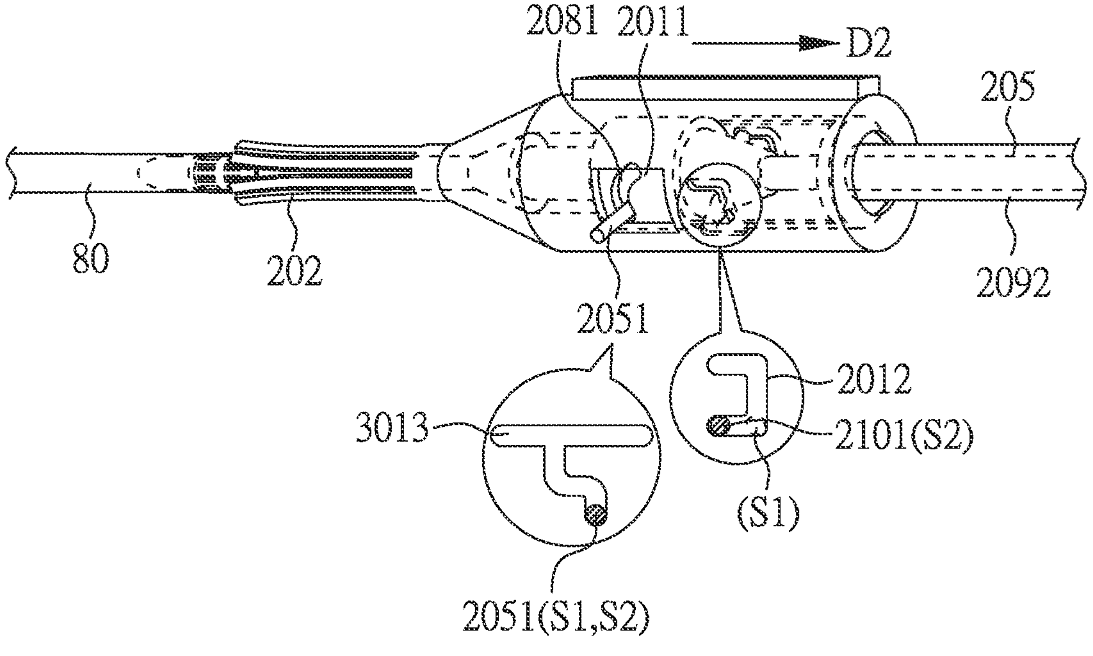

As shown in FIG. 9, as well as FIGS. 7 to 8, at this moment, the blood vessel 80 is in the state of being sleeved, which corresponds to FIG. 2. By operating the first operating unit 501 (as shown in FIG. 18), the advancing member 209 moves along the direction D2, and the first tube 201 operatively connected with the advancing member 209 moves along the direction D2 synchronously. In addition, since the third tube 210 and the fourth tube 208 may move with respect to the first tube 201, the guiding rod 2101 and the cross rod 2051 move to the second position S2. On the other hand, as shown in FIG. 9 and FIG. 19, since the first button 5011 is connected with the first elastic element 5012, when the first button 5011 is not operated, the first elastic element 5012 may provide elastic force to retract the guiding rod 2101 and the cross rod 2051 to the first position S1, so that the vascular positioning member 202 clamps the blood vessel 80, which corresponds to FIG. 3. In more detail, by operating the first button 5011, the guiding rod 2101 and the cross rod 2051 may move back and forth between the first position S1 and the second position S2.

Figure 10:
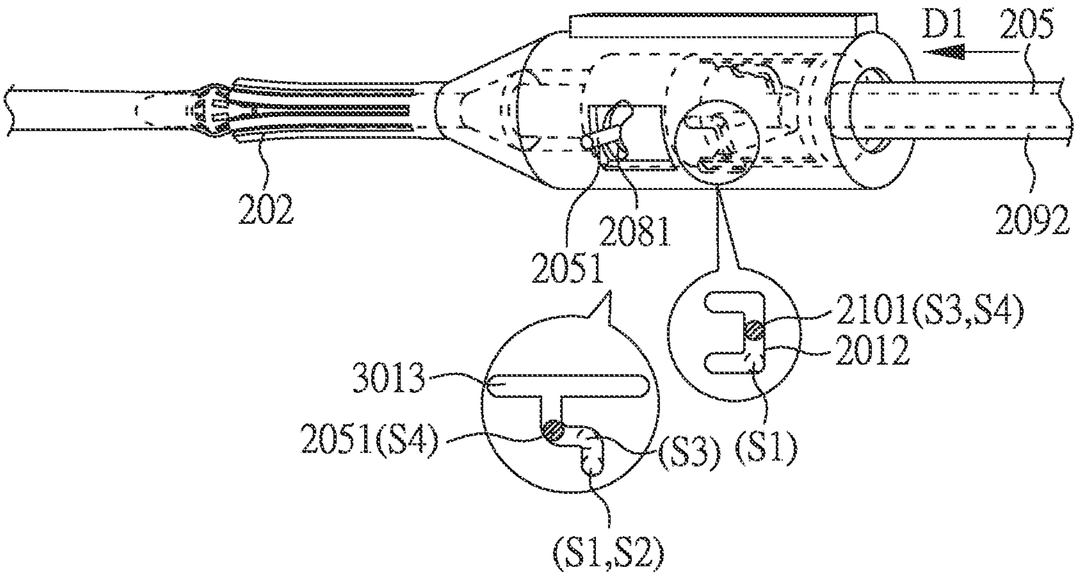

As shown in FIG. 10, as well as FIGS. 5 and 7, at this moment, the blood vessel 80 is in the state of being spread outward, which corresponds to FIG. 5. By operating the third operating unit 503 (as shown in FIG. 18), the third tube 208 moves along the direction D1, and the cross rod 2051 is rotated along the first through hole 2081, so that the guiding rod 2101 and the cross rod 2051 move from a position S1 to a third position S3. When the third tube 210 continues to move in the direction D1, the cross rod 2051 will move along the direction D1 by a distance "a" (as shown in FIG. 6), and the guiding rod 2101 is engaged with the first guiding rail 2012 to synchronously push the first tube 201 to move along the direction D1 by a distance "a" (as shown in FIG. 6), thereby moving from the third position S3 to the fourth position S4.

Figure 11:
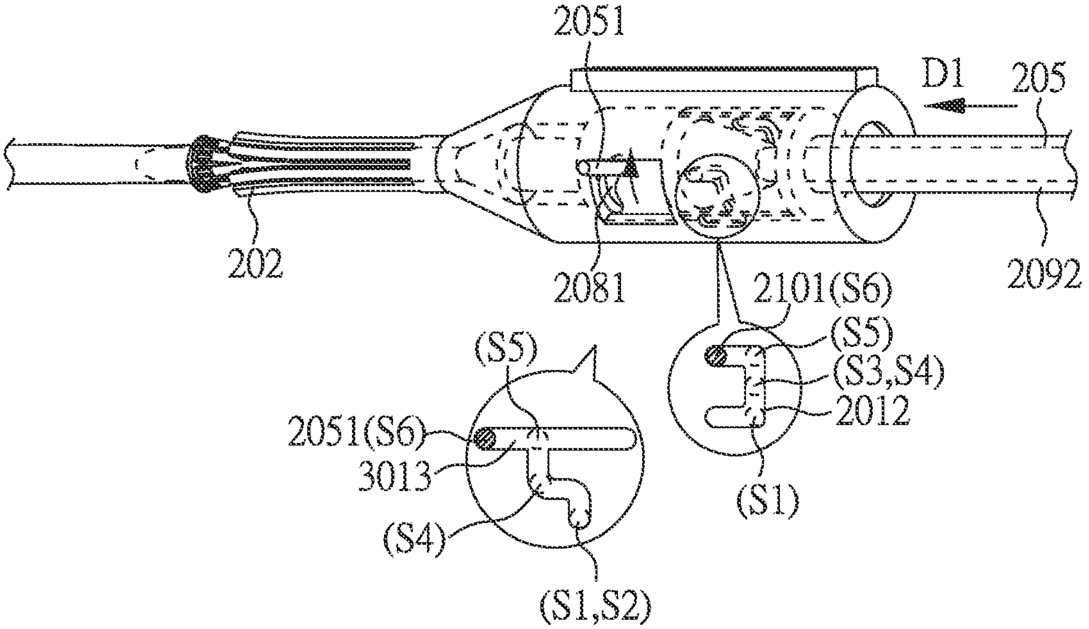

As shown in FIG. 11, as well as FIGS. 4, 7, 17 and 18, at this moment, the blood vessel 80 is in the state of being fastened to the vascular anastomosis ring 104, which corresponds to FIG. 6. By continuously operating the third operating unit 503, the third tube 210 continues to move along the direction D1, so that the guiding rod 2101 and the cross rod 2051 move from a fourth position S4 to a fifth position S5, and then to a sixth position S6, thereby fastening the blood vessel 80 to the vascular anastomosis ring 104. On the other hand, by pressing the fourth operating unit 504, the first linkage element 5045 and the first connecting member 3041 move along the direction D2, and the second tube 205 in the blood vessel 80 moves along the direction D2 synchronously, while the guiding rod 2101 and the cross rod 2051 are allowed to move from the sixth position S6 to a seventh position S7.

Actuating Mechanism of Vascular Anastomosis Assembly 30

FIGS. 13 to 17 are schematic diagrams illustrating the actuating mechanism of the vascular anastomosis assembly 30 according to an embodiment of the present invention.

As shown in FIG. 13, at this moment, the vascular anastomosis assembly 30 is in the state of not being actuated, which corresponds to FIG. 1 and FIG. 8. The cross rod 2051 assembled in the second guiding rail 3013 is disposed at the first position, and the first linkage element 5045 is assembled on the first connecting member 3041.

Figure 14:
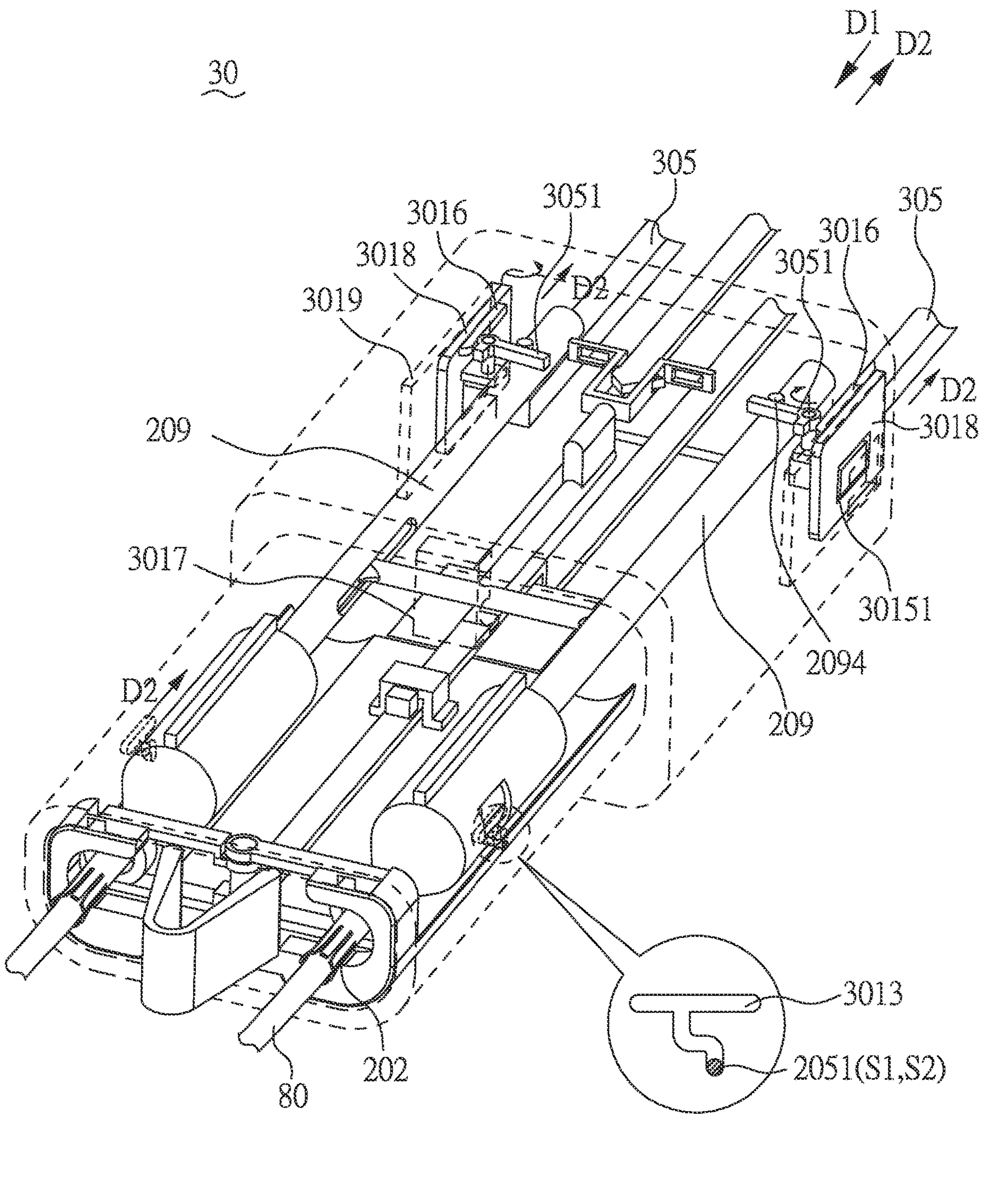

As shown in FIG. 14, as well as FIG. 12, at this moment, the blood vessel 80 is in the state of being sleeved, which corresponds to FIG. 2 and FIG. 9. By operating the first operating unit 501 (as shown in FIG. 18), the third driving member 305 moves along the direction D2, and the rotation element 3051 on the sliding member 3018 buckled with the third driving member 305 comes into touch with the second bump 3016 on housing 301 (as shown in FIG. 12), so that the rotation element 3051 is pivotally rotated to be engaged with the fourth hump 2094, thereby driving the third driving member 305 and the advancing member 209 collectively to move along the direction D2, and thus completing the step of making the blood vessel 80 sleeved.

Figure 15:
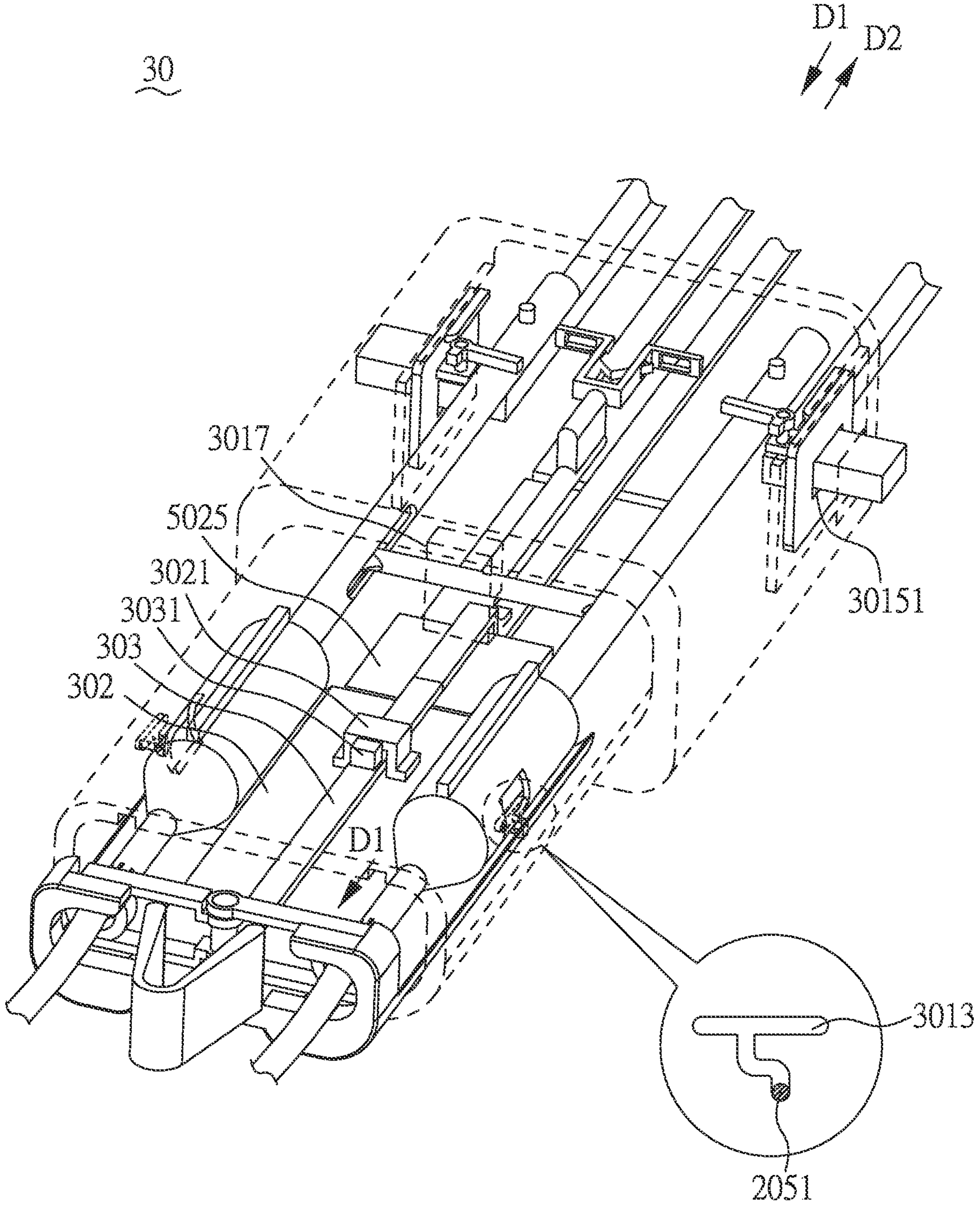

As shown in FIG. 15, as well as FIG. 12, at this moment, the blood vessel jaw unit 10 is in the state of being actuated, which corresponds to FIG. 4. By operating the second operating unit 502 (as shown in FIG. 18), the fourth driving member 5025 moves along the direction D1 and pushes the base 302. In addition, since the first protruding portion 3021 arranged on the base 302 is operatively connected with the third bump 3031, the first driving member 303 also synchronously moves along the direction D1, so that the blood vessel jaw unit 10 moves to be positioned.

Figure 16:
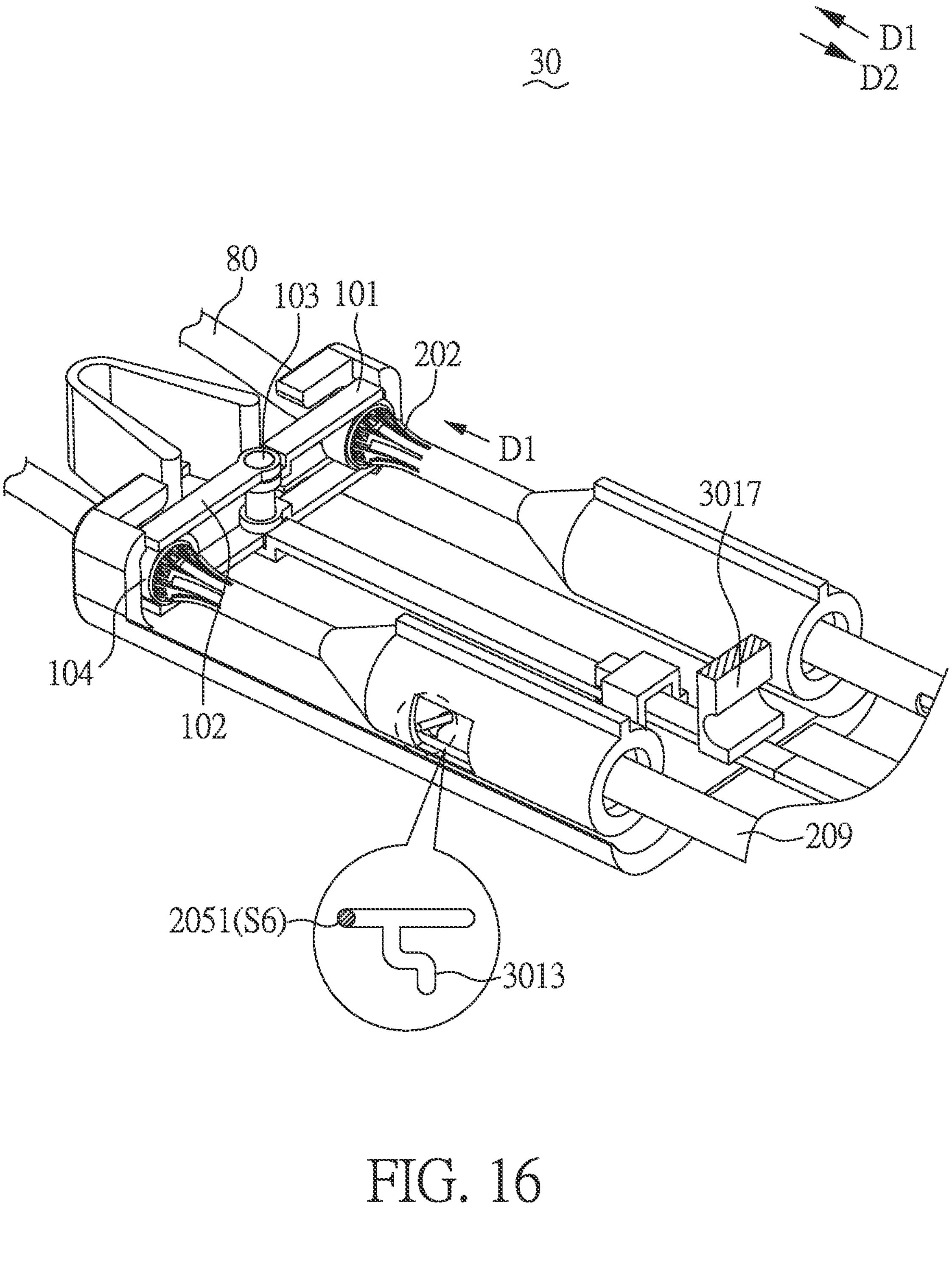

As shown in FIG. 16, as well as FIG. 4, at this moment, the blood vessel 80 is in the state of being fastened to the vascular anastomosis ring 104, which corresponds to FIGS. 6 and 11. By operating the third operating unit 503 (as shown in FIG. 18), the advancing member 209 moves along the direction D1, so that the cross rod 2051 assembled in the second guiding rail 3013 moves to the sixth position S6, and the blood vessel 80 is fastened on the vascular anastomosis ring 104.

Figure 17:
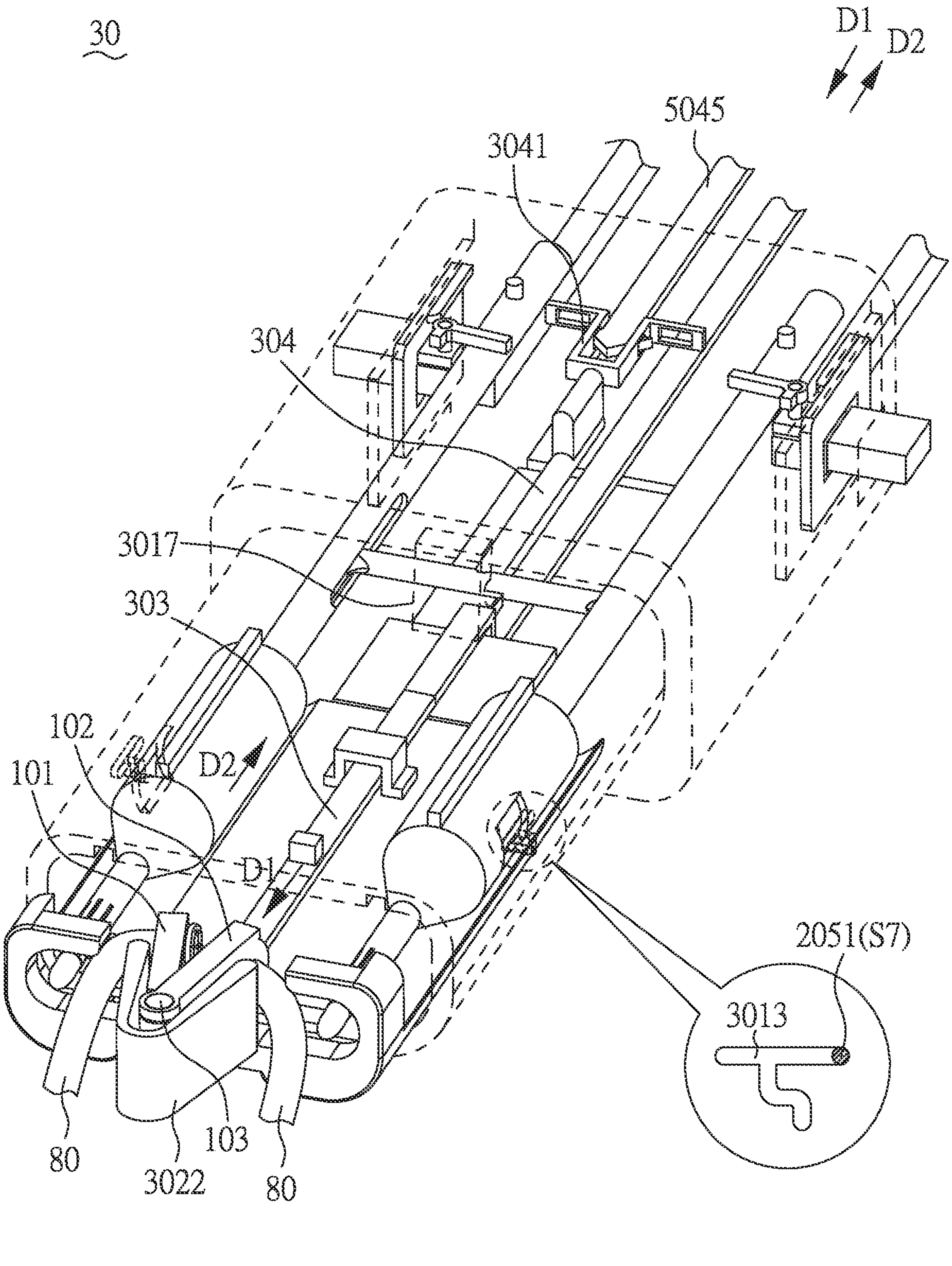

As shown FIG. 17, as well as FIG. 12, at this moment, it is in that state of performing anastomosis on the fastened blood vessel 80. By operating the fourth operating unit 504 (as shown in FIG. 18), the first linkage element 5045 moves along the direction D2, and is operatively connected with the second driving member 304 through the first connecting member 3041, so that the second tube 205 disposed in the blood vessel and the first tube 201 move along the direction D2 away from the vascular anastomosis ring 104 (as shown in FIG. 7), thereby enabling the cross rod 2051 to reach the seventh position S7, while the first driving member 303 moves along the direction D1. Since the first portion 101 and the second portion 102 of the vascular jaw unit 10 correspond to the clamping and positioning unit 3022, the vascular jaw unit 10 performs pivotal rotation by taking the pivot member 103 as the pivot axis, and the first portion 101 and the second portion 102 are clamped toward each other and arranged in the recess 3023 of the base 302, so as to complete the step of anastomosis of the blood vessel 80. In this embodiment, the blood vessel 80 that has been anastomosed may be separated from the vascular anastomosis assembly 30 from the top of the recess 3023.

The actuating mechanism of the operating assembly 50 and the release assembly 60

FIG. 19 is a perspective view of the first operating unit 501 according to an embodiment of the present invention.

FIG. 20 is a perspective view of the second operating unit 502 according to an embodiment of the present invention.

FIG. 21 is a perspective view of the third operating unit 503 according to an embodiment of the present invention.

FIG. 22 is a perspective view of the fourth operating unit according to an embodiment of the present invention.

As shown in FIG. 19, by operating the first button 5011, the first button 5011 moves along the direction D2 and the first elastic element 5012 is compressed by force. Furthermore, by taking the fourth through hole 50143 as a pivot axis, the third fastening member 50131 assembled in the second through hole 50141 and the second connecting rod 5014 are used to drive the fourth fastening member 3052 assembled in the third through hole 50142, so that the fourth fastening member 3052 and the third driving member 305 move along the direction D2 synchronously thereby making the blood vessel 80 sleeved (as shown in FIGS. 2, 9 and 14), When the first button 5011 is not operated, the first elastic element 5012 provides elastic force to move the third driving member 305 and the first button 5011 along the direction D1, thereby clamping the blood vessel 80 (as shown in FIG. 2).

As shown in FIG. 20, by operating the second holding member 5021, the second holding member 5021 moves along the direction D2. Furthermore, by taking the fifth fastening member 5023 assembled in the sixth through hole 50212 as a pivot axis, the sixth fastening member 50251 assembled in the seventh through hole 50213 is used to drive the fourth driving member 5025 to move along the direction D1, and the fourth driving member 5025 is connected with the base 302 (as shown in FIG. 15), so that the vascular anastomosis ring 104 may move along the direction D1 for being positioned (as shown in FIG. 4). In addition, in this embodiment, when the second holding element 5021 is operated, the third holding element 5031 will be slowly approached to the handle synchronously (as shown in FIG. 21), so as to facilitate subsequent operations.

As shown in FIG. 21, the third holding element 5031 is operated to move the third holding element 5031 along the direction D2 and, by taking the seventh fastening member 5033 assembled in the ninth through hole 50312 as a pivot axis, the eighth fastening member 2096 enters the tenth through hole 50313 from the fourth opening 50314, thereby driving the sixth tube 5038 to move along the direction D1. Because the sixth tube 5038 is connected with the advancing member 209, the advancing member 209 moves along the direction D1, thereby fastening the blood vessel 80 to the vascular anastomosis ring 104 (as shown in FIG. 5). In addition, when the third holding element 5031 is operated, since the advancing member 209 continues to move along the direction D1, the engaging member 5036 will contact the displacement control member 401, and the engaging member 5036 will be turned over to release the tenon 50361, so that the fifth tube 5035 does not move with the advancing member 209, thereby allowing the fourth holding element 5041 to be operated continuously (as shown in FIG. 22). On the other hand, when the vascular anastomosis assembly 30 is replaced (as shown in FIG. 12), the sixth elastic element 5037 will reset the third holding element 5031 and make the tenon 50361 return to its original position. In addition, in this embodiment, while the third holding element 5031 is operated, the fourth holding element 5041 will be slowly approached to the handle synchronously (as shown in FIG. 22), so as to facilitate subsequent operations.

As shown in FIG. 22, the fourth holding element 5041 is operated to move along the direction D2 and is rotated by taking the ninth fastening member 5050 assembled in the eleventh through hole 50411 as a pivot axis, so that the toothed structure 50413 on the fourth holding element 5041 meshes with the first gear 5042. The toothed structure 50413 moves along the direction D1 (i.e., clockwise rotation if observing the viewing angle of the drawing) to drive the first gear 5042, the second gear 5043, the third gear 5044 and the fourth gear 5051 to rotate synchronously along the direction D2 (i.e., counterclockwise rotation if observing the viewing angle of the drawing), thereby driving the first linkage element 5045 to move along the direction D2 and further driving the second linkage element 5046 to move along the direction D1 so as to achieve the purpose of anastomosis of the blood vessel 80. Since the fourth holding element 5041 needs to move back and forth for many times, when the fourth holding element 5041 moves along the direction D2 (i.e., when operating the fourth holding element 5041), the first gear 5042 may rotate, and when the fourth holding element 5041 moves along the direction D1 (i.e., when releasing the fourth holding element 5041), the first gear 5042 does not drive the fourth gear. In addition, since the first locking element 50471 meshes with the second gear 5043, and the fourth gear 5051 meshes with the second locking element 5052, when the release assembly 60 is not operated, the fourth gear 5051, the second gear 5043 and the third gear 5044 are only allowed to rotate in one direction, whereby the fourth holding element 5041 may be actuated back and forth multiple times to slowly combine the two vascular anastomotic rings 104 visually so as to complete the anastomosis of the blood vessel 80 (as shown in FIG. 17). Moreover, the fourth holding element 5041 is pressed to the utmost, thereby releasing the first linkage element 5045 from the first connecting member 3041. After the blood vessel 80 that has been anastomosed visually is separated from the vascular anastomosis component 30 from above the recess 3023, the third button 4021 may be pressed to remove the vascular anastomosis assembly 30 (as shown in FIG. 12). When the release assembly 60 is operated, the second button 601 is pressed to move the fifth fastening base 50474 upward, and the adjustment element 50472 may move upward, so that the first locking element 50471 is loosened and does not mesh with the second gear 5043, thereby allowing the first gear 5042, the second gear 5043 and the third gear 5044 to be restored to the state that the fourth holding element 5041 is not operated, and releasing the second holding element 5021 the third holding element 5031 and the fourth holding element 5041 for reset. As a result, the first linkage element 5045 and the second linkage element 5046 that are respectively connected with the seventh elastic element 5048 and the eighth elastic element 5049 are restored to the state that the fourth holding element 5041 is not operated, so that a new vascular anastomotic assembly 30 may be connected to successively anastomose another blood vessel.

In view of the foregoing, by using the vascular anastomosis device of the present invention, it is able to effectively improve the fastening effect of vascular anastomosis, shorten the operation time, increase the convenience, or perform vessel joining through simple steps, thereby reducing the burden on the surgeon or lowering the additional risk of surgery.

The aforementioned embodiments are examples only for convenience of description. The scope of the present disclosure is claimed hereinafter in the claims and is not limited to the embodiments.

What is claimed is:

1. A vascular anastomosis device, comprising:

a vascular jaw unit provided with a vascular anastomosis ring; and a first vascular fastening component, wherein the vascular anastomosis ring is sleeved on the first vascular fastening component, and the first vascular fastening component includes:

a first tube having a first end and a second end opposite to the first end, wherein the first tube is provided with a first opening and a first guiding rail;

a vascular positioning member connected with the first end of the first tube;

a second tube accommodated in the first tube;

a vascular supporting unit assembled on the second tube and arranged adjacent to a third end of the vascular positioning member, the third end being opposite to the first end of the first tube, wherein the vascular supporting unit includes a vascular supporting body and a vascular spreading member, and the vascular spreading member is assembled on the vascular supporting body;

an advancing member accommodated in the first tube, wherein the advancing member is arranged adjacent to the second end of the first tube; and a third tube accommodated in the advancing member and provided with a cross rod and a guiding rod, wherein the cross rod is arranged corresponding to the first opening of the first tube, and the guiding rod is arranged corresponding to the first guiding rail.

2. The vascular anastomosis device as claimed in claim 1, wherein the vascular positioning member is provided with a first protrusion at the third end, the vascular spreading member is provided with a first concave hole, and the first concave hole is arranged corresponding to the first protrusion.

3. The vascular anastomosis device as claimed in claim 1, wherein the vascular jaw unit includes a first portion and a second portion pivotally connected with the first portion through a pivot member, the vascular anastomosis ring is arranged on the first portion, and another vascular anastomosis ring is arranged on the second portion.

4. The vascular anastomosis device as claimed in claim 3, further comprising another first vascular fastening component, wherein said another first vascular anastomosis ring is sleeved on said another first vascular fastening component.

5. The vascular anastomosis device as claimed in claim 1, wherein the first vascular fastening component further includes: a fourth tube provided with a first through hole, wherein the cross rod is assembled in the first through hole of the fourth tube and protrudes from the first opening of the first tube.

6. The vascular anastomosis device as claimed in claim 1, further comprising: a housing accommodated therein the vascular jaw unit and the first vascular fastening component.

7. The vascular anastomosis device as claimed in claim 6, wherein the housing is provided with a second guiding rail arranged corresponding to the cross rod.

8. The vascular anastomosis device as claimed in claim 6, wherein the housing is provided with a third guiding rail, a first bump is provided on the first tube, and the third guiding rail is arranged corresponding to the first bump.

9. The vascular anastomosis device as claimed in claim 8, further comprising: a base accommodated in the housing and provided with a clamping and positioning unit, wherein the vascular jaw unit is arranged corresponding to the clamping and positioning unit.

10. The vascular anastomosis device as claimed in claim 9, wherein the vascular jaw unit includes a first portion and a second portion pivotally connected with the first portion through a pivot member, the clamping and positioning unit includes a recess, and the first portion and the second portion are accommodated in the recess when the first portion and the second portion are clamped.

11. The vascular anastomosis device as claimed in claim 9, further comprising: a first driving member arranged on the base, wherein the vascular jaw unit is pivoted on the first driving member.

12. The vascular anastomosis device as claimed in claim 11, wherein the first driving member is provided with a third bump arranged corresponding to a first protruding portion of the base.

13. The vascular anastomosis device as claimed in claim 6, further comprising: a device body, wherein the housing includes a first fastening member and is assembled in the device body through the first fastening member.

14. The vascular anastomosis device as claimed in claim 13, further comprising: a fifth tube accommodated in the device body, wherein the fifth tube is provided with an engaging member.

15. The vascular anastomosis device as claimed in claim 14, further comprising: a displacement control member accommodated in the device body, wherein the displacement control member is arranged corresponding to the engaging member.

16. The vascular anastomosis device as claimed in claim 1, further comprising: a second driving member assembled in a sliding slot of the advancing member.

17. The vascular anastomosis device as claimed in claim 1, further comprising: a third driving member provided with a second protrusion arranged corresponding to a sliding member, and the sliding member is pivoted with a rotation element, wherein the rotation element is arranged corresponding to a fourth bump of the advancing member.

* * * * *